US006228888B1

(12) United States Patent
Slusher

(10) Patent No.: US 6,228,888 B1
(45) Date of Patent: May 8, 2001

(54) METHODS FOR TREATING ANXIETY, ANXIETY DISORDERS AND MEMORY IMPAIRMENT USING NAALADASE INHIBITORS

(75) Inventor: Barbara S. Slusher, Kingsville, MD (US)

(73) Assignee: Guilford Pharmaceuticals Inc., Baltimore, MD (US)

(*) Notice: Subject to any disclaimer, the term of this patent is extended or adjusted under 35 U.S.C. 154(b) by 0 days.

(21) Appl. No.: 09/345,782

(22) Filed: Jul. 1, 1999

(51) Int. Cl.$^7$ .......................... A61K 31/19; A61K 31/195
(52) U.S. Cl. ............................................ 514/574; 514/562
(58) Field of Search ..................................... 514/574, 562

(56) References Cited

U.S. PATENT DOCUMENTS

| 5,143,908 | 9/1992 | Parsons et al. ...................... 514/114 |
| 5,464,819 | 11/1995 | Suzuki .................................. 514/16 |
| 5,672,592 | 9/1997 | Jackson et al. . |
| 5,795,877 | 8/1998 | Jackson et al. . |
| 5,804,602 | 9/1998 | Slusher et al. . |
| 5,824,662 | 10/1998 | Slusher et al. . |
| 5,863,536 | 1/1999 | Jackson et al. . |
| 5,880,112 | 3/1999 | Jackson et al. . |
| 5,902,817 | 5/1999 | Jackson et al. . |

FOREIGN PATENT DOCUMENTS 651-91  2/1998  (CL).

OTHER PUBLICATIONS

Smith et al., "Progesterone alters GABA and glutamate responsiveness: a possible mechanism for its anxiolytic action," Brain Research (abstract), 1987, 400(2), 353–59.
Stephens et al., "Does the Excitatory Amino Acid Receptor Antagonist 2–APH Exhibit Anxiolytic Activity," Psychopharmacology (abstract), 1986, 90(2), 166–69.
Koek et al., "Use of a Conflict Procedure in Pigeons to Characterize Anxiolytic Drug Activity: Evaluation of N–methyl–D–aspartate Antagonists," Life Science (abstract), 1991, 49(9), 37–42.
Kehne et al., "NMDA Receptor Complex Antagonists have Potential Anxiolytic Effects as Measured with Separation- –Induced Ultrasonic Vocalizations," Eur. J. Pharmacol. (abstract), 1991, 193(3), 283–92.
Turski et al., "Relief of Experimental Spasticity and Anxiolytic/Anticonvulsant Actions of the alpha–amino–3–hydroxy–5–methyl–4–isoxazolepropionate Antagonist 2,3–dihydroxy–6–nitro–7–sulfamoyl–benzo (F) quinoxaline," J. Pharmacol.Exp.Ther (abstract), 1992, 260(2), 742–47.
Chojnacka–Wojcik et al., "The Anxiolytic–like Effect of Metabotropic Glutamate Receptor Antagonists after Intra- –hippocampal Injection in Rats," Eur. J. Pharmacol. (abstract), 1997, 319 (2–3), 153–56.

Chojnacka–Wojcik et al., "Anxiolytic–like Effects of Matabotropic Glutamate Antagonist (RS)–alpha–methylsyerine–O–phosphate in Rats," Pol. J. Pharmacol. (abstract), 1996, 48(5), 507–09.
Karreman et al., "Effect of a Pharmacological Stressor on Glutamate Efflux in the Prefrontal Cortex," Brain Res. (abstract), 1996, 716(1–2), 180–82.
Kehne et al., "MDL 100,458 and MDL 102,288: Two Potent and Selective Glycine Receptor Antagonists with Different Functional Profiles," Eur. J. Pharmacol. (abstract), 1995, 284(1–2), 109–18.
Altamura et al., "Plasma and Platelet Excitatory Amino Acids in Psychiatric Disorders," Am. J. Psychiatry (abstract), 1993, 150(11), 1731–33.
Potter et al., "NAALADase Inhibition at Neuroprotective Doses Spares Cognition in Normal Rodents," Society for Neuroscience 28$^{th}$ Annual Meeting, Session 93.6., 1998.
Shimada et al., "Spermidine Potentiates Dizocilpine–induced Impairment of Learning Performance by Rats in a 14–unit T–Maze," European J. of Pharmacol., 1994, 263, 293–300.
Spangler et al., "Thrombosis of Parietal, but not Striate, Cortex Impairs Acquisition of a 14–Unit T–Maze in the Rat," Physiology & Behavior, 1994, 56, 95–101.
Jaarsma et al., "N–acetylaspartate and N–acetylaspartylglutamate Levels in Alzheimer's Disease Post–Mortem Brain Tissue," J. Neurol. Sci., 1994, 127, 230–33.
Wiley, "Behavioral Pharmacology of N–methyl–D–aspartate Antagonists: Implications for the Study and Pharmacotherapy of Anxiety and Schizophrenia," Exp. Clin. Psychopharmocol. (abstract), 1997, 5(4), 365–74.
Sajdyk et al., "Excitatory Amino Acid Receptor Antagonists Block the Cardiovascular and Anxiety Responses elicited by Gamma–Aminobutyric Acid A Receptor Blockade in the Basolateral Amygdala of Rats," J. Pharmacol. Exp. Ther. (abstract), 1997, 1998, 283(2), 969–77.
Helton et al., "Anxiolytic and Side–Effect Profile of LY354740: A Potent, Highly Selective, Orally Active Agonist for Group II Metabotropic Glutamate Receptors," J. Pharmacol. Exp. Ther. (abstract), 1998, 284(2), 651–60.
Monn et al., "Design, Synthesis, and Pharmacological Characterization of (=)–2–aminobicyclo[3.1.0]hexane–2,6–dicarboxylic acid (LY354740): A Potent, Selective, and Orally Active Group 2 Metabotropic Glutamate Receptor Agonist Possessing Anitconvulsant and Anxiolytic Properties," J. Med. Chem. (abstract), 1997, 40(4), 528–37.
Matheus et al., "Antagonism of Non–NMDA Receptors in the Dorsal Periaqueductal Grey Induces Anxiolytic Effect in the Elevated Plus Maze," Psychopharmacology (abstract), 1997, 132 (1), 14–18.

(List continued on next page.)

Primary Examiner—William R. A. Jarvis
(74) Attorney, Agent, or Firm—Lyon & Lyon LLP

(57) ABSTRACT

The present invention relates to methods of using NAALADase inhibitors for treating glutamate-mediated diseases, disorders and conditions selected from the group consisting of anxiety, anxiety disorders and memory impairment.

10 Claims, No Drawings

OTHER PUBLICATIONS

Sajdyk et al., "Excitatory Amino Acid Receptors in the Basolateral Amygdala Regulate Anxiety Responses in the Social Interaction Test," *Brain Res.* (abstract), 1997, 764 (1–2), 262–64.

Taylor et al., "A Summary of Mechanistic Hypotheses of Gabapentin Pharmacology," *Epilepsy Res.* (abstract), 1998, 29(3), 233–49.

Kotlinska et al., "The Putative AMPA Receptor Antagonist, LY326325, Produces Anxiolytic–like Effects without Altering Locomotor, Activity in Rats," *Pharmacol. Biochem. Behav.* (abstract), 1998, 60(1), 119–24.

Kretschmer et al., "Riluzole, A Glutamate Release Inhibitor, and Motor Behavior," *Naunyn Schmiedebergs Arch Pharmacol.* (abstract), 1998, 358(2):181–90.

METHODS FOR TREATING ANXIETY, ANXIETY DISORDERS AND MEMORY IMPAIRMENT USING NAALADASE INHIBITORS

BACKGROUND OF THE INVENTION

The present invention relates to pharmaceutical compositions and methods for treating glutamate-mediated diseases, disorders and conditions, particularly anxiety, anxiety disorders and memory impairment, using NAALADase inhibitors.

Anxiety disorders afflict over 23 million Americans. These people are tormented by panic attacks, obsessive thoughts, flashbacks, nightmares or countless frightening physical symptoms. Classes of drugs which are prescribed for the treatment of anxiety disorders include the benzodiazepines (such as diazepam) and buspirone hydrochloride. Although the benzodiazepines have achieved widespread acceptance since their introduction in the 1960's, their use is restricted due to their adverse side effects, in particular their tendency to induce dependence. While lacking the dependence-inducing side effects of the benzodiazepines, buspirone hydrochloride has a slow onset of action (about 4 weeks). Thus, there is a need for new pharmaceutical compositions and methods for treating anxiety and anxiety disorders.

Excessive activation of glutamate receptors has been implicated in anxiety and anxiety disorders. Significantly higher glutamate plasma levels have been detected in patients with mood disorders than in comparison subjects. In social interaction tests on rats, the blocking of basal glutamate excitation elicited anxiolytic-like effects.

It is widely published that glutamate modulators possess anxiolytic properties. In animal models of anxiolytic activity, NMDA antagonists reduced separation-induced ultrasonic vocalizations in rat pups, antagonized the suppressive effects of punishment on locomotor activity in the four-plate test on mice, enhanced exploration in the open arms of an elevated plus maze by rats, and blocked anxiety responses elicited by GABAA receptor blockade in the basolateral amygdala of rats; AMPA/kainate antagonists increased the percentage of entries of rats into the open arms of an elevated plus maze, and caused a dose-dependent increase of punished drinking behavior in a conflict-suppressed drinking test on rats; AMPA antagonists normalized pathologically increased electromyogram (EMG) activity in the hind limb extensor muscles of rats; mGluR antagonists produced a dose-dependent anticonflict effect in a conflict drinking Vogel test on rats; and mGluR agonists exhibited anxiolytic effects on mice in the fear potentiated startle and elevated plus maze models.

Studies also suggest that the pharmacological effect of anxiolytic agents is mediated through the glutamatergic system. In an intact neuronal circuit of a model extrahypothalamic CNS area, systemic injection and local application of progesterone suppressed glutamate excitation. Microdialysis shows that anxiogenic beta-carboline significantly increases glutamate efflux in the prefrontal cortex of rats. Reports also indicate that the anxiolytic effects of riluzole are mediated by the blockade of glutamate transmission. Concordantly, the inhibition of glutamate synthesis has been proposed as a possible mechanism for the anxiolytic activity of gabapentin.

Excessive activation of glutamate receptors has also been implicated in neurodegenerative disorders (e.g., Alzheimer's disease, Huntington's disease and AIDS encephalopathy) and in the generation of long-term potentiation, which is regarded as an electrophysiological manifestation of learning and memory. Specifically, the NMDA subtype of glutamate receptor appears to be involved in learning processes because the NMDA antagonist 2-amino-5-phosphono-pentanoate (AP5) selectively impairs learning and blocks long-term potentiation in rats. It has thus been proposed that deterioration in glutamatergic systems might account for impairment in cognitive function observed in aged animals or in Alzheimer's disease.

Recent studies have implicated NAALADase in the pathogenesis of glutamate-mediated disorders. Lesion studies on rat and neuropathological studies on post-mortem tissue from patients with amyotrophic lateral sclerosis (ALS) indicate large decreases of N-acetylaspartate (NAA) and N-acetylaspartylglutamate (NAAG) tissue concentrations occurring in association with neuronal degeneration, and increases of NAA and NAAG in cerebal spinal fluid (CSF) from patients with ALS. Concordantly, abnormal NAAG levels and NAALADase activity have also been observed in post-mortem prefrontal and limbic brain tissue of schizophrenic patients.

Autopsy studies also suggest a strong correlation between NAAG/NAA and Alzheimer's disease. In post-mortem brain tissue, NAA and NAAG levels were found to be selectively decreased in brain areas (hippocampus and amygdala) affected by Alzheimer's disease pathology.

Although not limited to any one particular theory, it is believed that NAALADase inhibitors block glutamate release pre-synaptically. The inventors have discovered that the glutamate blocking activity of NAALADase inhibitors has direct therapeutic applications for the pharmacotherapy of glutamate-mediated diseases, disorders and conditions, including without limitation anxiety, anxiety disorders and neurodegenerative diseases. Since neurodegenerative diseases are one of the leading causes of memory impairment, the inventors theorize that NAALADase inhibitors may be also beneficial in the treatment of memory impairment.

Most research and development activity to date have focused on blocking post-synaptic glutamate receptors with compounds such as NMDA antagonists, glycine antagonists, and other post-synaptic excitatory amino acid (EAA) receptor blockers. Unfortunately, these agents produce severe toxicities even under normal conditions, thus limiting their clinical use.

By contrast, NAALADase inhibitors inhibit glutamate release presynaptically without interacting with post-synaptic glutamate receptors. Since NAALADase inhibitors do not appear to alter basal glutamate levels, they may be devoid of the behavioral toxicities associated with post-synaptic glutamate antagonists.

Until a few years ago, only a few NAALADase inhibitors had been identified and they were used in non-clinical research. Examples of these compounds include general metallopeptidase inhibitors such as o-phenanthroline, metal chelators such as EGTA and EDTA, and peptide analogs such as quisqualic acid and β-NAAG. These compounds either have toxic side effects or are incapable of being administered in pharmaceutically effective amounts. In view of the broad range of potential applications, there is a need for new NAALADase inhibitors and pharmaceutical compositions and methods of using the same.

SUMMARY OF THE INVENTION

The present invention relates to a method for treating a glutamate mediated disease, disorder or condition selected from the group consisting of anxiety, anxiety disorder and memory impairment, comprising administering an effective amount of a NAALADase inhibitor to a mammal in need of such treatment.

The present invention also relates to a pharmaceutical composition comprising:

(i) an effective amount of a NAALADase inhibitor for treating a glutamate mediated disease, disorder or condition selected from the group consisting of anxiety, anxiety disorder and memory impairment; and (ii) a pharmaceutically acceptable carrier.

DETAILED DESCRIPTION OF THE INVENTION

Definitions

"Compound 1" refers to pure and impure forms of 2-(2-sulfanylethyl)pentanedioic acid, or the compound prepared by Example 23.

"Compound 2" refers to 2-[[(2,3,4,5,6-pentafluorobenzyl) hydroxyphosphinyl]methyl]-pentanedioic acid.

"Compound 3" refers to 2-(phosphonomethyl)-pentanedioic acid (PMPA).

"Effective amount" refers to the amount required to produce the desired effect. "Therapeutically effective amount" refers to the amount required to treat anxiety, anxiety disorders and memory impairment.

"Isosteres" refer to elements, molecules or ions having similar or identical physical properties. Typically, two isosteric molecules have similar or identical volumes and shapes. Ideally, isosteric compounds should be isomorphic and able to co-crystallize. Among the other physical properties that isosteric compounds usually share are boiling point, density, viscosity and thermal conductivity. However, certain properties are usually different: dipolar moments, polarity, polarization, size and shape since the external orbitals may be hybridized differently. The term "isosteres" encompass "bioisosteres".

"Carboxylic acid isosteres" include without limitation direct derivatives such as hydroxamic acids, acyl-cyanamide and acylsulfonamides; planar acidic heterocycles such as tetrazoles, mercaptoazoles, sulfinylazoles, sulfonylazoles, isoxazoles, isothiazoles, hydroxythiadiazole and hydroxychromes; and nonplanar sulfur- or phosphorus-derived acidic functions such as phosphinates, phosphonates, phosphonamides, sulphonates, sulphonamides, and acylsulphonamides. *The Practice of Medicinal Chemistry*, Academic Press, 1996.

"Metabolite" refers to a substance produced by metabolism or by a metabolic process.

"Pharmaceutically acceptable equivalent" includes without limitation pharmaceutically acceptable salts, hydrates, metabolites, prodrugs and carboxylic isosteres. Many pharmaceutically acceptable equivalents are expected to have similar or the same in vitro or in vivo activity as the compounds of formulas I–VI.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalene-sulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. Also, the basic nitrogen-containing groups can be quarternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Pharmaceutically acceptable prodrug" refers to a derivative of the inventive compounds which undergoes biotransformation prior to exhibiting its pharmacological effect (s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995), or methods readily apparent to one skilled in the art. For example, the inventive compounds can be transformed into prodrugs by converting one or more of the hydroxy or carboxy groups into esters.

"Alkyl" refers to a branched or unbranched saturated hydrocarbon chain comprising a designated number of carbon atoms. For example, a $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, a $C_2$–$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 6 carbon atoms.

"Halo" or "halogen" refers to fluoro, chloro, bromo and iodo, unless otherwise indicated.

"Isomers" refer to compounds having the same number and kind of atoms, and hence the same molecular weight, but differing in respect to the arrangement or configuration of the atoms.

"Stereoisomers" refer to compounds which have identical chemical constitution, but differ as regards to the arrangement of the atoms or groups in space.

"Optical isomers" refer to either of two kinds of stereoisomers. One kind is represented by mirror-image structures called enantiomers, which result from the presence of one or more asymmetric carbon atoms in the compound (glyceraldehyde, lactic acid, sugars, tartaric acid, amino acids). The other kind is exemplified by diastereoisomers, which are not mirror images. These occur in compounds having two or more asymmetric carbon atoms; thus, such compounds have $2_n$ optical isomers, where n is the number of asymmetric carbon atoms.

"Enantiomers" refer to stereoisomers which are non-superimposable mirror images of one another.

"Enantiomer-enriched" refers to a mixture in which one enantiomer predominates.

"Racemic" refers to a mixture containing equal parts of individual enantiomers.

"Non-racemic" refers to a mixture containing unequal parts of individual enantiomers.

"Animal" refers to a living organism having sensation and the power of voluntary movement and requirement for its existence oxygen and organic food. Examples include without limitation a mammal such as a member of the human, equine, porcine, bovine, murine, canine or feline species. In the case of a human, the term "animal" may also be referred to as a "patient".

"Disease" refers to any deviation from or interruption of the normal structure or function of any part, organ, or system (or combination thereof) of the body that is manifested by a characteristic set of symptoms and signs and whose etiology, pathology, and prognosis may be known or unknown. *Dorland's Illustrated Medical Dictionary*, W.B. Saunders Co., 27th ed. (1988).

"Disorder" refers to any derangement or abnormality of function; a morbid physical or mental state. *Dorland's Illustrated Medical Dictionary*, W.B. Saunders Co., 27th ed. (1988).

"Anxiety" includes without limitation the unpleasant emotion state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. *Dorland's Illustrated Medical Dictionary*, W.B. Saunders Co., 27th ed. (1988).

"Anxiety Disorder" includes without limitation mental disorders in which anxiety and avoidance behavior predominate. *Dorland's Illustrated Medical Dictionary*, W.B. Saunders Co., 27th ed. (1988). Examples include without limitation panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS. Other anxiety disorders are characterized in *Diagnostic and Statistical Manual of Mental Disorders* (American Psychiatric Association 4th ed. 1994). The skilled artisan will recognize that there are alternative nomenclatures, nosologies, and classification systems for pathologic psychological conditions and that these systems evolve with medical scientific progress.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin ($B_2$, thiamine and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Mental disorder" refers to any clinically significant behavioral or psychological syndrome characterized by the presence of distressing symptoms or significant impairment of functioning. Mental disorders are assumed to result from some psychological or organic dysfunction of the individual; the concept does not include disturbances that are essentially conflicts between the individual and society (social deviance).

"Treating" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and/or (iii) relieving the disease, disorder or condition, i.e., causing regression of the disease, disorder and/or condition.

In relation to memory impairment, "treating" refers to:

(i) preventing memory impairment from occurring in an animal which may be predisposed to memory impairment but has not yet been diagnosed as having it;

(ii) inhibiting memory impairment, i.e., arresting its development;

(iii) relieving memory impairment, i.e., causing its regression; and/or (iv) enhancing memory.

"Enhancing memory performance" refers to improving or increasing the mental faculty by which to register, retain or recall past experiences, knowledge, ideas, sensations, thoughts or impressions.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-acetylated α-linked acidic dipeptidase, a membrane-bound metallopeptidase which catabolizes NAAG to N-acetylaspartate ("NAA") and glutamate ("GLU"):

Catabolism of NAAG by NAALADase

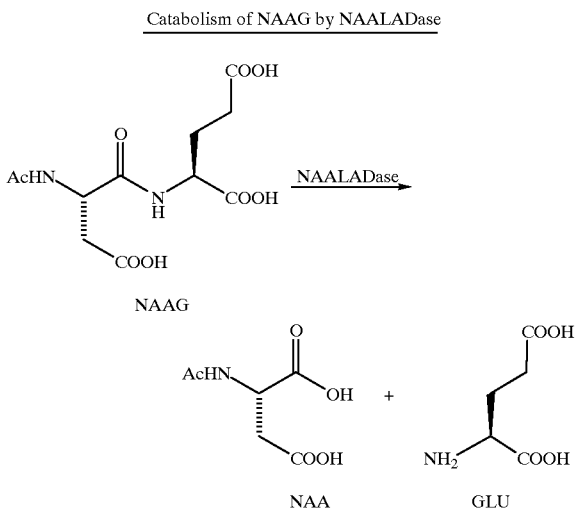

Based upon amino acid sequence homology, NAALADase has been assigned to the M28 peptidase family. NAALADase is also called prostate specific membrane antigen (PSM) or human glutamate carboxypeptidase II (GCP II) EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG's synaptic action. Alternatively, if NAAG functions as a precursor for glutamate, the primary function of NAALADase may be to regulate synaptic glutamate availability.

"NAALADase inhibitor" refers to any compound which inhibits NAALADase enzyme activity.

"Inhibition", in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound which is required to cause a 50% inhibition of the target enzyme.

"Acid containing metal chelator" refers to any compound having (i) a functional group capable of interacting with the metal(s) at the active site of the NAALADase enzyme; and (ii) an acid portion which interacts at the recognition site of the NAALADase enzyme.

METHODS OF USE

The present invention relates to a method for treating a glutamate mediated disease, disorder or condition selected from the group consisting of anxiety, anxiety disorder and memory impairment, comprising administering an effective amount of a NAALADase inhibitor to a mammal in need of such treatment.

Anxiety disorders treatable by the inventive methods include without limitation mental disorders in which anxiety and avoidance behavior predominate, such as panic attack, agoraphobia, panic disorder, acute stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS.

Memory impairments treatable by the inventive methods include without limitation diminished mental registration, retention or recall of past experiences, knowledge, ideas, sensations, thoughts or impressions.

PHARMACEUTICAL COMPOSITIONS

The present invention further relates to a pharmaceutical composition comprising:

(i) an effective amount of a NAALADase inhibitor for treating a glutamate mediated disease, disorder or condition selected from the group consisting of anxiety, anxiety disorder and memory impairment; and (ii) a pharmaceutically acceptable carrier.

The pharmaceutical composition may further comprise at least one additional therapeutic agent.

PREFERRED NAALADASE INHIBITORS

Although not limited to any one particular theory, it is believed that the NAALADase inhibitors used in the inventive methods and pharmaceutical compositions modulate levels of glutamate by acting on a storage form of glutamate which is hypothesized to be upstream from the effects mediated by the NMDA receptor.

A preferred NAALADase inhibitor is a compound of formula I:

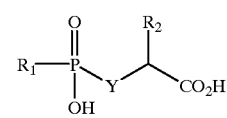

I or a pharmaceutically acceptable equivalent, wherein:

Y is $CR_3R_4$, $NR_5$ or O;

$R_1$ is selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl, Ar, COOR, $NR_6R_7$ and OR, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, COOR, $NR_6R_7$ and Ar;

$R_2$ is selected from the group consisting of hydrogen, $C_1$–$C_6$ alkyl, $C_2$–$C_6$ alkenyl, $C_3$–$C_8$ cycloalkyl, $C_5$–$C_7$ cycloalkenyl, Ar, halo and carboxy, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, $NR_6R_7$ and Ar;

$R_3$ and $R_4$ are independently hydrogen or $C_1$–$C_3$ alkyl;

$R_5$ is hydrogen or $C_1$–$C_3$ alkyl;

R, $R_6$ and $R_7$ are independently selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl and Ar, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl and phenyl, wherein said Ar is unsubstituted or substituted with one or more substituent (s) independently selected from the group consisting of halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, carboxy and $NR_1R_2$.

Preferably, Y is $CH_2$.

More preferably, when Y is $CH_2$, then $R_2$ is —$(CH_2)_2$COOH.

Most preferably, when Y is $CH_2$ and $R_2$ is —$(CH_2)_2$COOH, then $R_1$ is hydrogen, $C_1$–$C_4$ alkyl, $C_2$–$C_4$ alkenyl, $C_3$–$C_8$ cycloalkyl, $C_5$–$C_7$ cycloalkenyl, benzyl, phenyl or OR, wherein said alkyl, alkenyl, cycloalkyl, cycloalkenyl, benzyl and phenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, $NR_6R_7$, benzyl and phenyl.

Preferred compounds of formula I are selected from the group consisting of:

2-(phosphonomethyl)pentanedioic acid;

2-[[(2-carboxyethyl)hydroxyphosphinyl]methyl]-pentanedioic acid;

2-[(benzylhydroxyphosphinyl) methyl]pentanedioic acid;

2 -[(phenylhydroxyphosphinyl) methyl]pentanedioic acid;

2-[[((hydroxy)phenylmethyl)hydroxyphosphinyl]-methyl]pentanedioic acid;

2-[(butylhydroxyphosphinyl)methyl]pentanedioic acid;

2-[[(3-methylbenzyl)hydroxyphosphinyl)methyl]-pentanedioic acid;

2-[(3-phenylpropylhydroxyphosphinyl) methyl]-pentanedioic acid;

2-[[(4-fluorophenyl)hydroxyphosphinyl]methyl]-pentanedioic acid;

2-[(methylhydroxyphosphinyl) methyl]pentanedioic acid;

2-[(phenylethylhydroxyphosphinyl)methyl]-pentanedioic acid;

2-[[(4-methylbenzyl)hydroxyphosphinyl]methyl]-pentanedioic acid;

2-[[(4-fluorobenzyl)hydroxyphosphinyl]methyl]-pentanedioic acid;

2-[[(4 -methoxybenzyl) hydroxyphosphinyl]methyl]-pentanedioic acid;

2-[[(3-trifluoromethylbenzyl)hydroxyphosphinyl]-methyl]pentanedioic acid;

2-[[4-trifluoromethylbenzyl)hydroxyphosphinyl]-methyl]pentanedioic acid;

2-[[(2-fluorobenzyl)hydroxyphosphinyl]methyl]-pentanedioic acid;

2-[[(2,3,4,5,6-pentafluorobenzyl)hydroxy-phosphinyl]methyl]pentanedioic acid; and pharmaceutically acceptable equivalents.

More preferably, the compound of formula I is 2-[(2,3,4,5,6-pentafluorobenzyl) hydroxyphosphinyl]-methyl] pentanedioic acid or a pharmaceutically acceptable equivalent. Most preferably, the compound of formula I is an enantiomer or an enantiomer-enriched mixture.

Representative compounds of formula I wherein $R_1$ is substituted with COOR include without limitation:

2-[[2-carboxypropyl)hydroxyphosphinyl]methyl]-pentanedioic acid;

2-[[2-carboxybutyl)hydroxyphosphinyl]methyl]-pentanedioic acid;

2-[[(2-carboxypentyl)hydroxyphosphinyl]methyl]-pentanedioic acid;

2-[[(2-carboxy-3-phenylpropyl)hydroxyphosphinyl]-methyl]pentanedioic acid;

2-[[2-carboxy-3-naphthylpropyl)hydroxy-phosphinyl]-methyl]pentanedioic acid;

2-[[2-carboxy-3-pyridylpropyl)hydroxyphosphinyl]-methyl]pentanedioic acid;

2-[[2-benzyloxycarbonyl)-3-phenylpropyl)hydroxy-phosphinyl]methyl]pentanedioic acid;

2-[[2-methoxycarbonyl)-3-phenylpropyl)hydroxy-phosphinyl]methyl]pentanedioic acid;

2-[[(3-carboxy-2-methoxycarbonyl)propyl)hydroxy-phosphinyl]methyl]pentanedioic acid;

2-[[(4-carboxy-2-methoxycarbonyl) butyl) hydroxy-phosphinyl]methyl]pentanedioic acid; and pharmaceutically acceptable equivalents.

Representative compounds of formula I wherein $R_1$ is substituted with $NR_6R_7$ include without limitation:

2-[({[benzylamino]benzyl}(hydroxyphosphinyl))-methyl]pentanedioic acid;

2-[({[carboxyamino]benzyl}(hydroxyphosphinyl))-methyl]pentanedioic acid;

2-[({[benzylamino]methyl}(hydroxyphosphinyl))-methyl]pentanedioic acid;

2-[({[acetylamino]methyl}(hydroxyphosphinyl))-methyl]pentanedioic acid;

2-[({[diphenylamino]methyl}(hydroxyphosphinyl))-methyl]pentanedioic acid;

2-[({[phenylamino]methyl}(hydroxyphosphinyl))-methyl]pentanedioic acid;

2-({[(phenylcarboxamido)methyl](hydroxy-phosphinyl)}methyl)pentanedioic acid;

2-({[(phenylsulfonamido)methyl](hydroxy-phosphinyl)}methyl)pentanedioic acid;

2-[({[(4-fluorophenyl)amino]methyl}(hydroxy-phosphinyl))methyl]pentanedioic acid;

2-[({[(4-methoxyphenyl)amino]methyl}(hydroxy-phosphinyl))methyl]pentanedioic acid;

2-[({[(4-methylphenyl)amino]methyl}-(hydroxyphosphinyl))methyl]pentanedioic acid;

2-[({[(4-tert-butylphenyl)amino]methyl}-(hydroxyphosphinyl))methyl]pentanedioic acid;

2-[({[(thioformanilido)amino]benzyl}-(hydroxyphosphinyl))methyl]pentanedioic acid;

2-[({[1,3-dioxo-2,3-dihydro-1H-2-isoindolyl]-methyl} hydroxyphosphinyl) methyl]pentanedioic acid; and pharmaceutically acceptable equivalents.

Another preferred NAALADase inhibitor is a compound of formula II

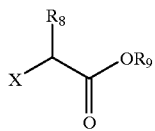

or a pharmaceutically acceptable equivalent, wherein:
X is a moiety of formula III, IV or V

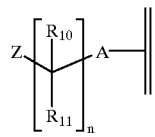

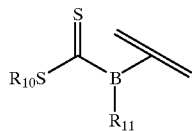

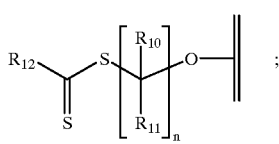

m and n are independently 0, 1, 2, 3 or 4;
Z is $SR_{13}$, $SO_3R_{13}$, $SO_2R_{13}$, $SOR_{13}$, $SO(NR_{13})R_{14}$ or $S(NR_{13}R_{14})_2R_{15}$;
B is N or $CR_{16}$;
A is O, S, $CR_{17}R_{18}$ or $(CR_{17}R_{18})_m S$;
$R_9$ and $R_{13}$ are hydrogen;
$R_8$, $R_{10}$, $R_{11}$, $R_{12}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and
$Ar_1$ is a carbocyclic or heterocyclic moiety, which is unsubstituted or substituted with one or more substituent(s);
provided that when X is a moiety of formula III and A is O, then n is 2, 3 or 4; when X is a moiety of formula III and A is S, then n is 2, 3 or 4; and when X is a moiety of formula III and A is $(CR_{17}R_{18})_m S$, then n is 0, 2, 3 or 4.

Possible substituents of said alkenyl, cycloalkyl, cycloalkenyl, and $Ar_1$ include without limitation $C_1$–$C_9$ alkyl, $C_2$–$C_9$ chain alkenyl, $C_1$–$C_9$ alkoxy, $C_2$–$C_9$ alkenyloxy, phenoxy, benzyloxy, $C_3$–$C_8$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

Representative compounds of formula II wherein X is a moiety of formula IV, $R_8$ is $-(CH_2)_2COOH$, $R_9$ is hydrogen, and B is $CR_{16}$, include without limitation:
2-(dithiocarboxymethyl)pentanedioic acid;
2-(1-dithiocarboxyethyl)pentanedioic acid; and
pharmaceutically acceptable equivalents.

Representative compounds of formula II wherein X is a moiety of formula IV, $R_8$ is $-(CH_2)_2COOH$, $R_9$ is hydrogen, and B is N, include without limitation:
2-dithiocarboxyaminopentanedioic acid;
2-[(N-methyldithiocarboxy) amino]pentanedioic acid; and
pharmaceutically acceptable equivalents.

Representative compounds of formula II wherein X is a moiety of formula V include without limitation:
2-benzyl-4-sulfanylbutanoic acid;
2-benzyl-4-sulfanylpentanoic acid;
2-(3-pyridylmethyl)-4-sulfanylpentanoic acid;
2-(3-pyridylmethyl)-4-sulfanylhexanoic acid;
2-benzyl-3-sulfanylpropanoic acid;
2-benzyl-3-sulfanylpentanoic acid;
2-(4-pyridylmethyl)-3-sulfanylpentanoic acid; and
pharmaceutically acceptable equivalents.

In a preferred embodiment of formula II, the NAALADase inhibitor is a compound of formula VI

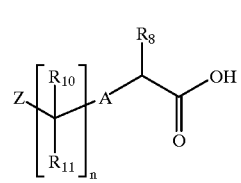

or a pharmaceutically acceptable equivalent, wherein:
n is 0, 1, 2 or 3;
Z is SH, $SO_3R_{13}$, $SO_2R_{13}$, $SOR_{13}$ or $S(NR_{13}R_{14})_2R_{15}$; and
A is O, S or $CR_{17}R_{18}$.
Preferably, Z is SH.
More preferably, when Z is SH, then $R_8$ is $-(CH_2)_2COOH$.
Preferred compounds of formula VI are selected from the group consisting of:
2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;

2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

More preferably, the compound of formula VI is selected from the group consisting of 2-(2-sulfanylethyl) pentanedioic acid, 2-(2-sulfanylpropyl)-pentanedioic acid, 2-(3-sulfanylpropyl)pentanedioic acid and pharmaceutically acceptable equivalents. Most preferably, the compound of formula VI is an enantiomer or an enantiomer-enriched mixture.

Other NAALADase inhibitors are described in U.S. Pat. Nos. 5,672,592, 5,795,877, 5,863,536 and 5,880,112, and allowed U.S. patent applications Ser. Nos. 08/825,997, 08/833,628, 08/835,572 and 08/842,360 for which the issue fees have been paid, the entire contents of which patents and applications are herein incorporated by reference.

The compounds used in the methods and pharmaceutical compositions of the present invention possess one or more asymmetric carbon center(s) and are thus capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the parent optically active drug is not necessary prior to dosing the patient since the compound can behave as a prodrug. The optically active compounds used in the inventive methods and pharmaceutical compositions can likewise be obtained by utilizing optically active starting materials.

It is understood that the compounds used in the inventive methods and pharmaceutical compositions encompass optical isomers as well as racemic and non-racemic mixtures.

SYNTHESIS OF NAALADASE INHIBITORS

Some of the NAALADase inhibitors used in the inventive methods and pharmaceutical compositions can be readily prepared by standard techniques of organic chemistry, utilizing the general synthetic pathways depicted in U.S. Pat. Nos. 5,672,592, 5,795,877, 5,863,536 and 5,880,112, and allowed U.S. patent applications Ser. Nos. 08/825,997, 08/833,628, 08/835,572 and 08/842,360 for which the issue fees have been paid, the entire contents of which patents and applications are herein incorporated by reference.

NAALADase inhibitors of formula I can be readily prepared by standard techniques of organic chemistry, utilizing the general synthetic pathways depicted below in Schemes I–IX. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995).

Scheme I

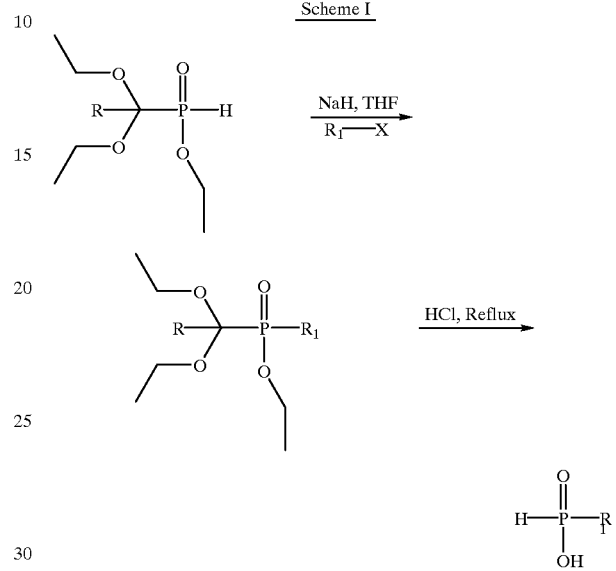

Methods of substituting the R groups are known in the art. Additional methods of synthesizing phosphinic acid esters are described in *J. Med. Chem.*, Vol. 31, pp. 204–212 (1988), and set forth below in Scheme II.

Scheme II

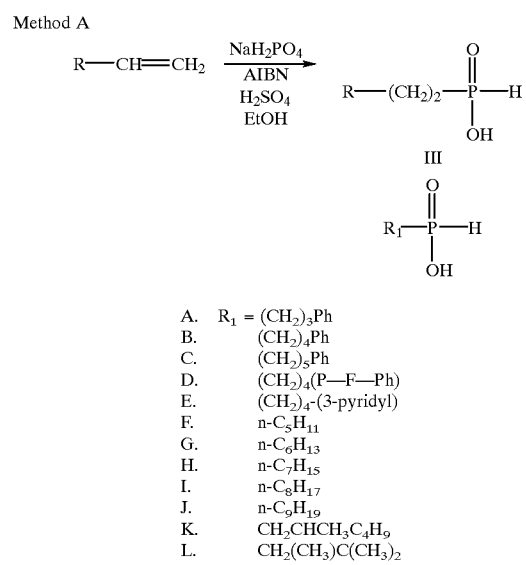

Scheme II -continued

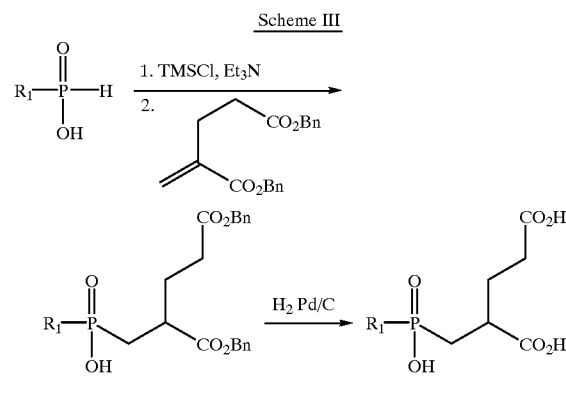

N. $R_1 = n\text{-}C_4H_9$
O. $CHCH_3C_5H_{11}$

Starting with the aforementioned phosphinic acid esters, there are a variety of routes for preparing the compounds of formula I. For example, a general route has been described in *J. Med. Chem.*, Vol. 39, pp. 619–622 (1996), and is set forth below in Scheme III.

Scheme III

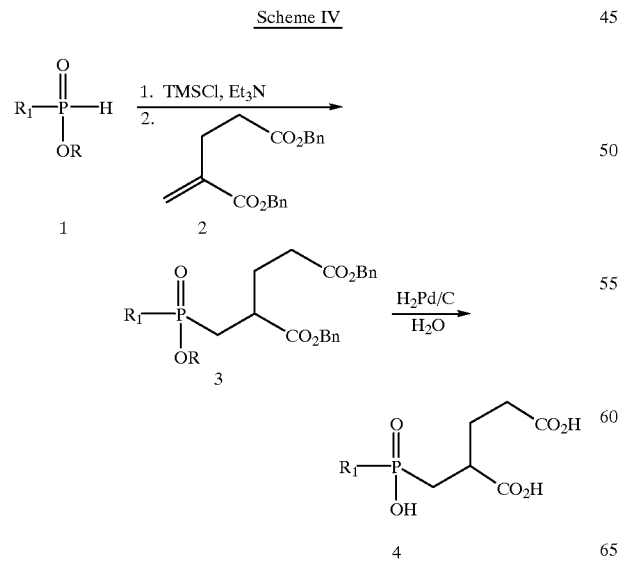

Other routes for preparing the compounds of formula I are set forth below in Scheme IV and Scheme V. Scheme IV and Scheme V show the starting material as a phosphinic acid derivative and the R group as any reasonable chemical substituent including without limitation the substituents listed in Scheme II and throughout the specification.

Scheme IV

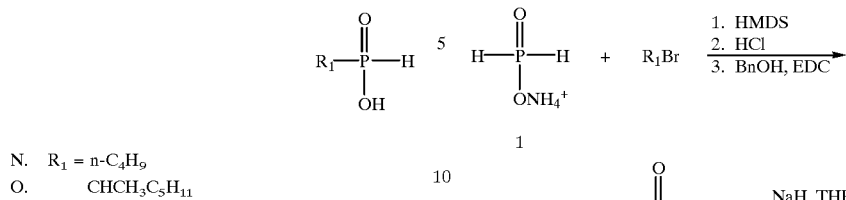

Scheme V

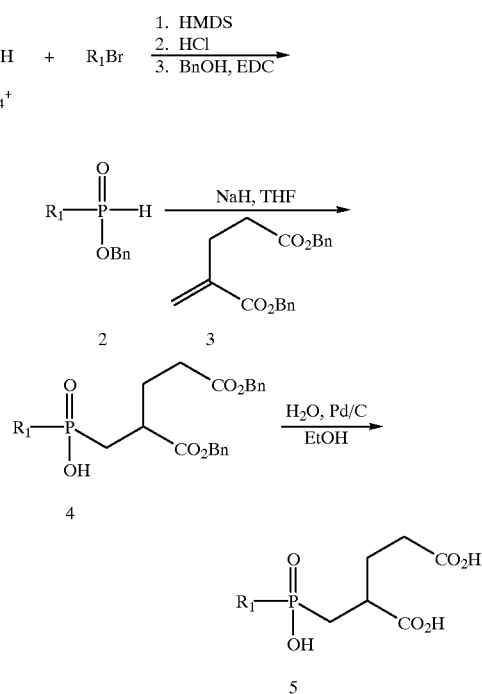

Another route for preparing the compounds of formula I allows for aromatic substitution at $R_1$, and is set forth below in Scheme VI.

Scheme VI

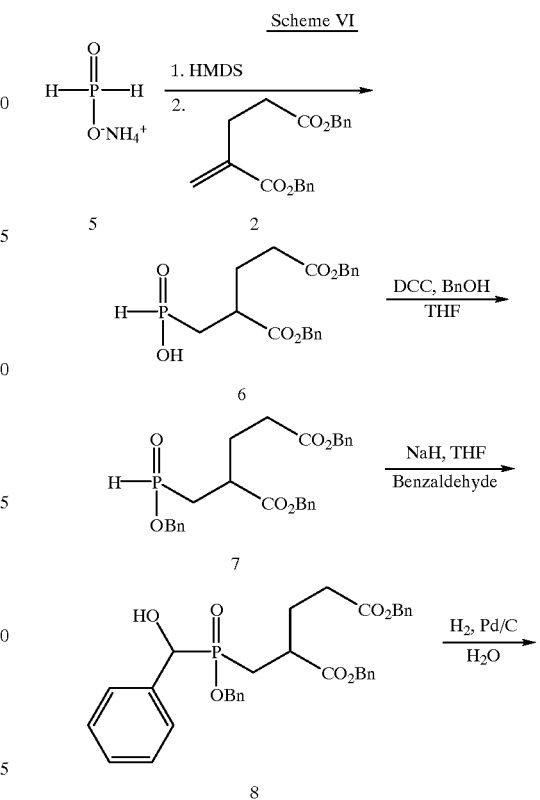

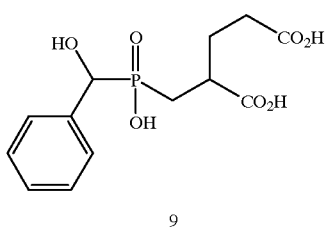

Another route for preparing the compounds of formula I allows for aromatic substitution at the $R_2$ position, and is set forth below in Scheme VII.

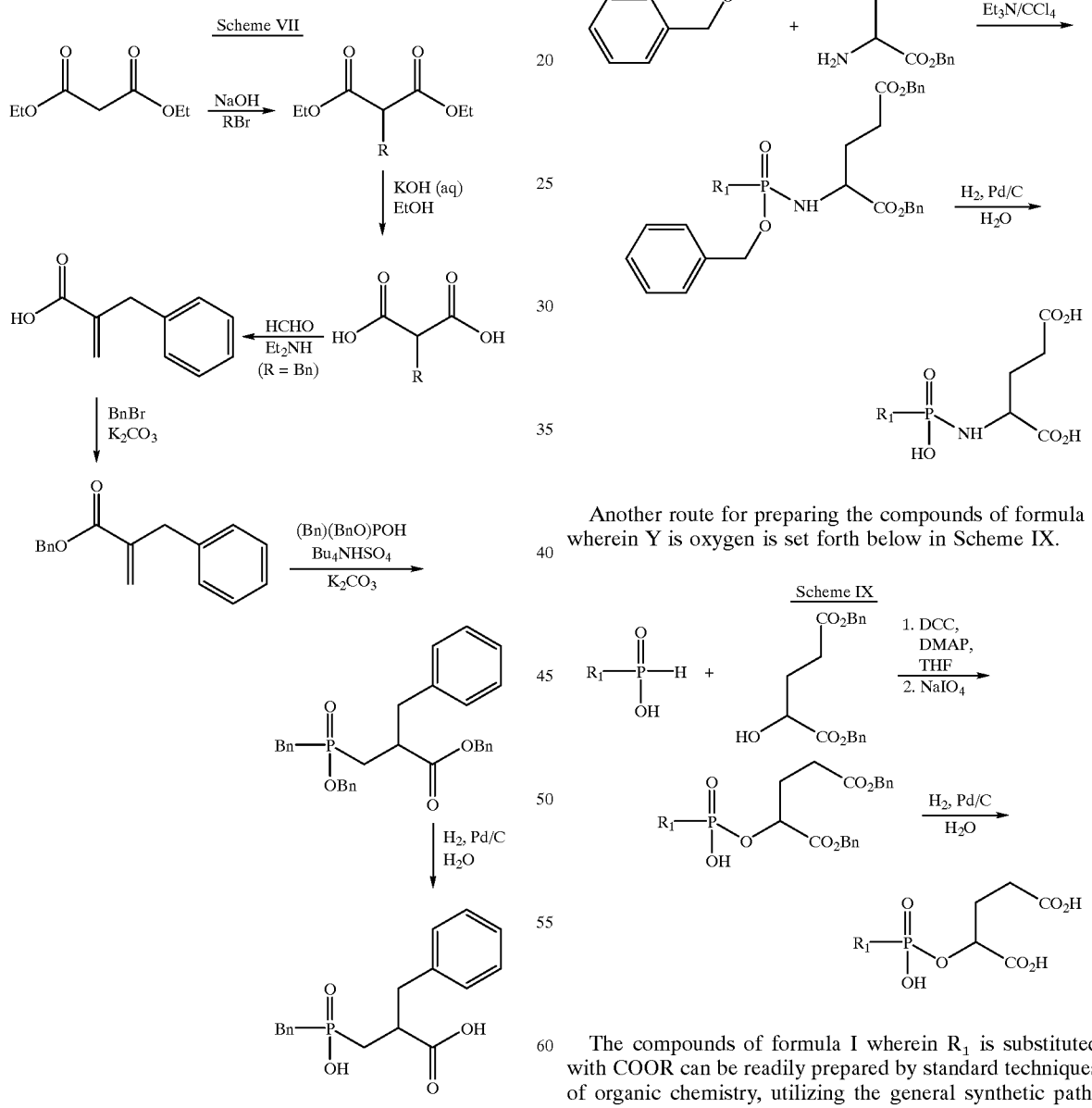

Another route for preparing the compounds of formula I wherein Y is $NR_5$ is set forth below in Scheme VIII.

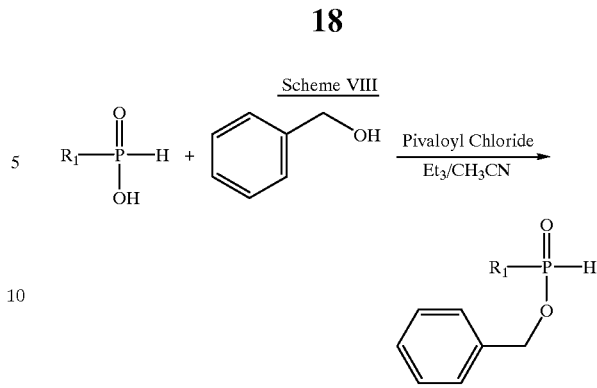

Another route for preparing the compounds of formula I wherein Y is oxygen is set forth below in Scheme IX.

The compounds of formula I wherein $R_1$ is substituted with COOR can be readily prepared by standard techniques of organic chemistry, utilizing the general synthetic pathways depicted below in Scheme X. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995).

Scheme X
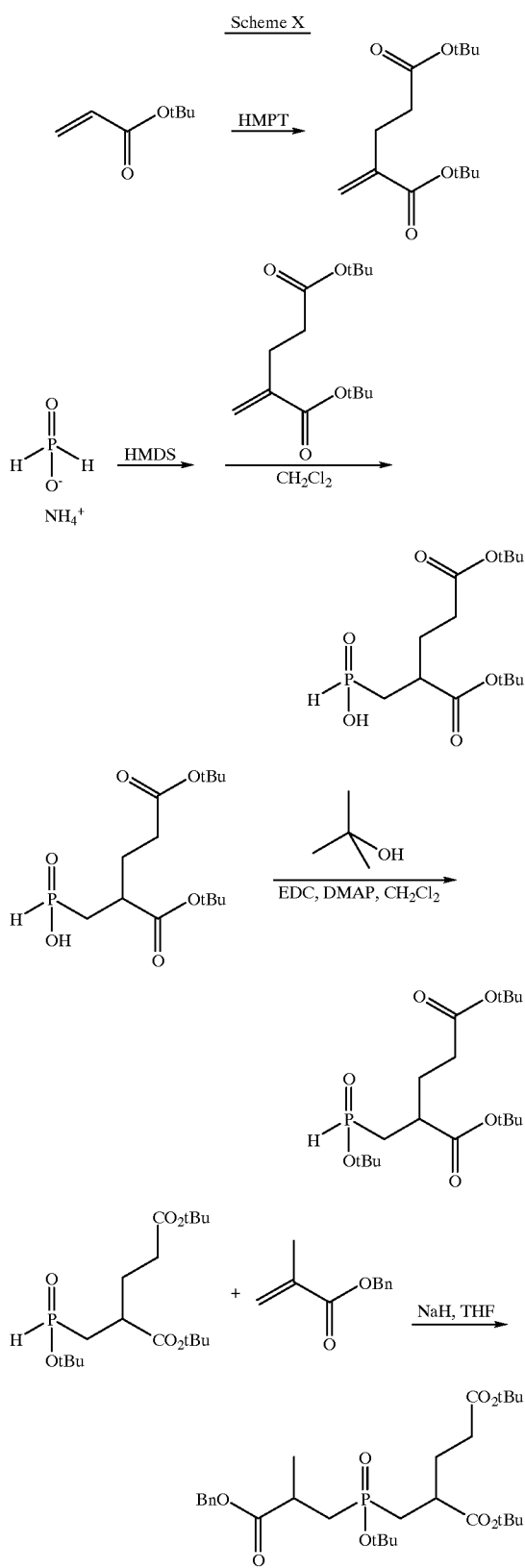
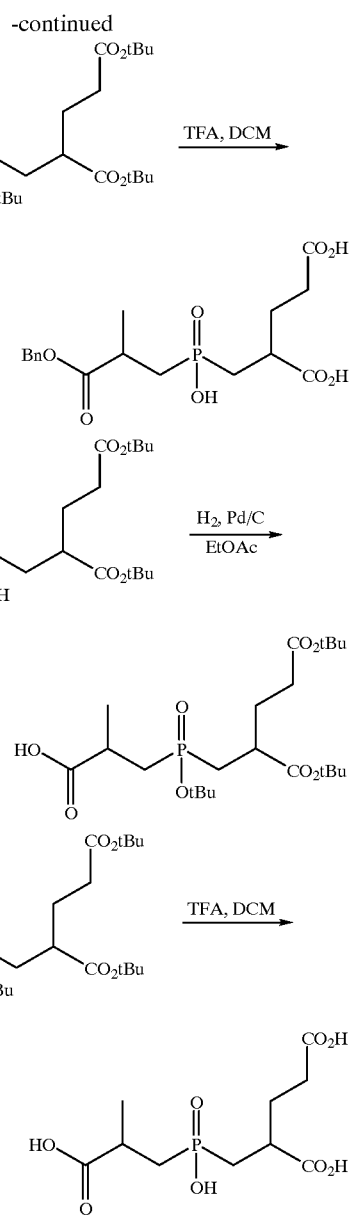
The compounds of formula I wherein $R_1$ is substituted with $NR_6R_7$ can be readily prepared by standard techniques of organic chemistry, utilizing the general synthetic pathways depicted below in Schemes XI and XII. Precursor compounds can be prepared by methods known in the art.
Scheme XI
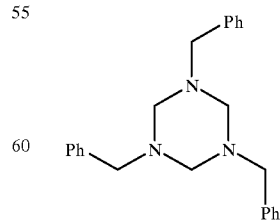
+

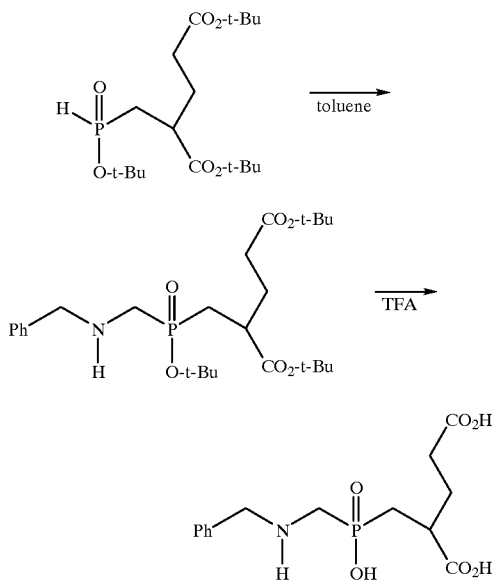
Scheme XII
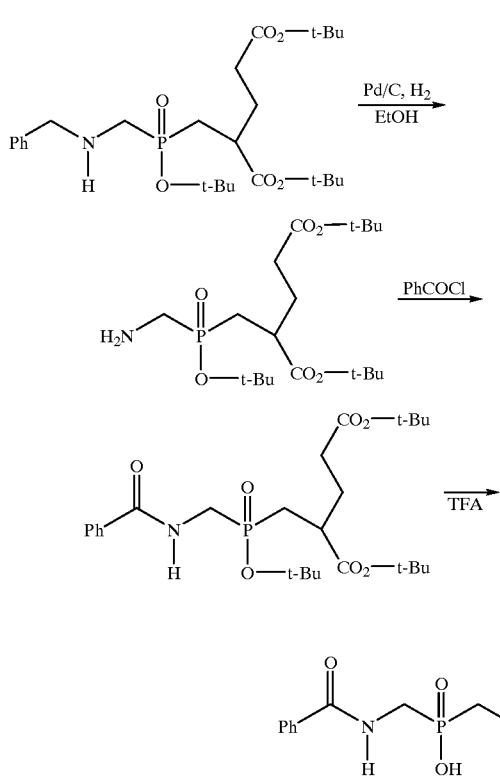
Scheme XIII
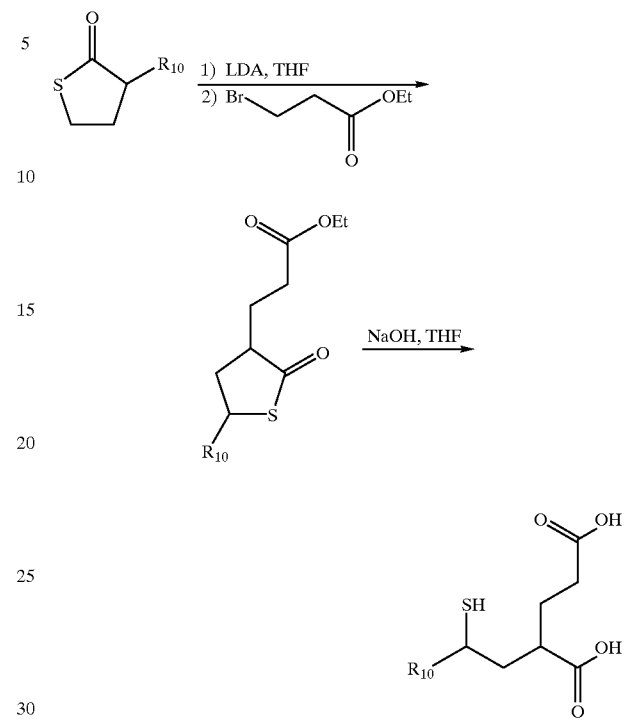
Scheme XIV
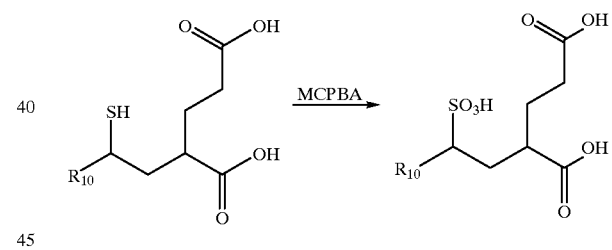
Scheme XV
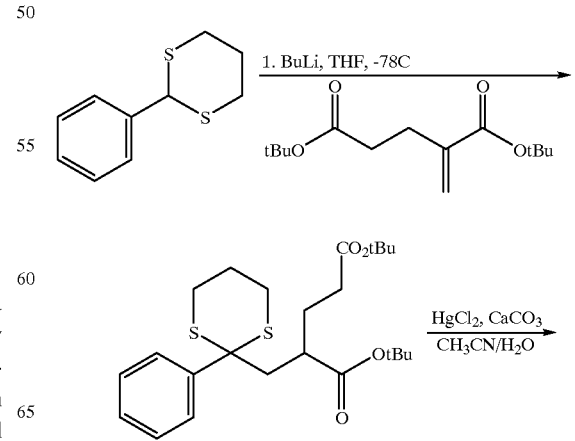
The NAALADase inhibitors of formula II wherein X is a moiety of formula III, and A is 0 or $CR_{17}R_{18}$ can be readily prepared by standard techniques of organic chemistry, utilizing the general synthetic pathways depicted below in Schemes XIII–XXII. Precursor compounds can be prepared by methods known in the art.

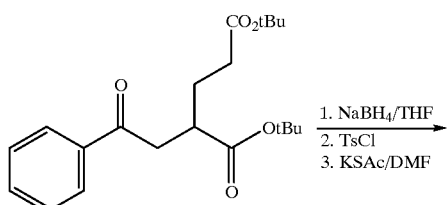
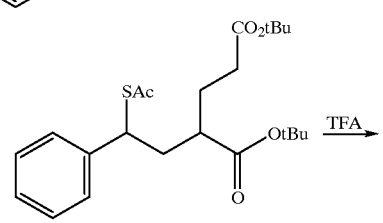
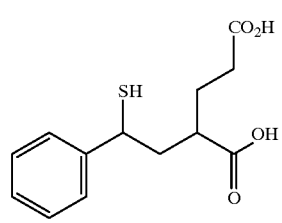
Scheme XVI
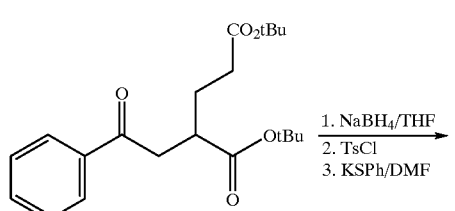
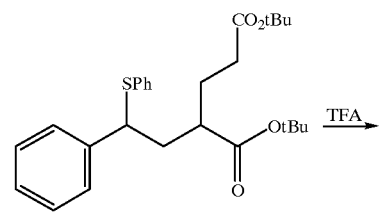
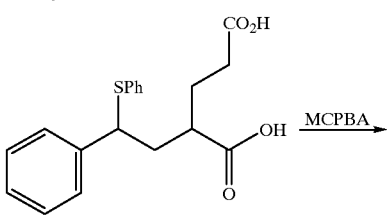
Scheme XVII
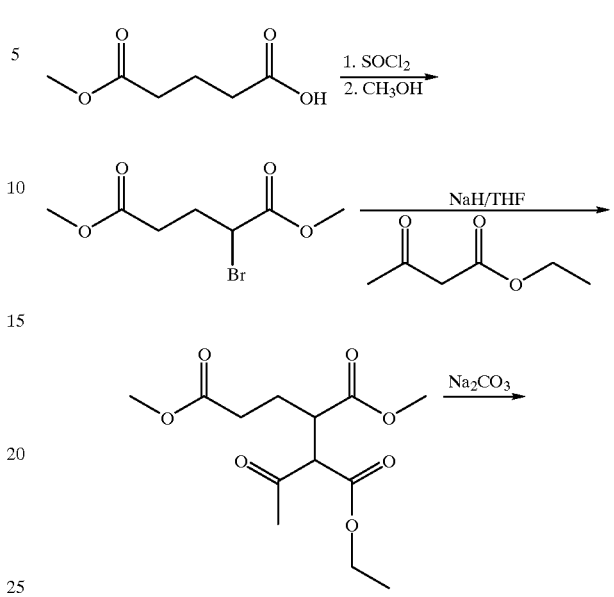
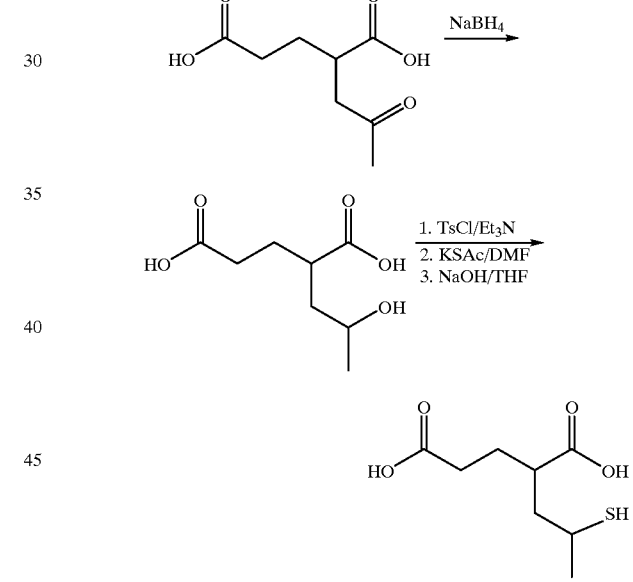
Scheme XVIII
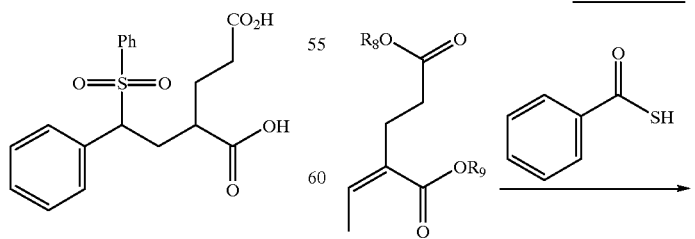

Scheme XIX

Reagents/steps shown:
1. TrtS(CH₂)₃CO₂H
2. NaBH₄, AcOH

→ (I) 5-[2-(tritylthio)ethyl]-2,2-dimethyl-1,3-dioxane-4,6-dione

Br(CH₂)₂COOCH₃ / NaOCH₃ →

(II) 5-(3-methoxy-3-oxopropyl)-5-[3-(tritylthio)propyl]-2,2-dimethyl-1,3-dioxane-4,6-dione NaOH →

(III) 2-(carboxy)-2-[3-(tritylthio)propyl]pentanedioic acid derivative

DMSO, Heat →

(IV) 2-[3-(tritylthio)propyl]pentanedioic acid (TrtS(CH₂)₃CH(CO₂H)CH₂CH₂CO₂H)

TFA, TIPS →

Intermediate: HS-CH(CH₃)-... (thiol acid intermediate)

2-methoxyethylamine applied to R₈O-/R₉O- benzoylthio protected diester →

Scheme XX

Dibenzyl 2-hydroxypentanedioate + 2,4,6-trimethyl-1,3,5-trithiane, Heat →

Dibenzyl 2-(1-mercaptoethoxy)pentanedioate (HS-CH(CH₃)-O-CH(CO₂Bn)CH₂CH₂CO₂Bn)

→ 2-(1-mercaptoethoxy)pentanedioic acid (HS-CH(CH₃)-O-CH(CO₂H)CH₂CH₂CO₂H)

(V) 2-(3-mercaptopropyl)pentanedioic acid (HS(CH₂)₃CH(CO₂H)CH₂CH₂CO₂H)

Scheme XXI 2-hydroxypentanedioic acid + CS₂ → 2-[(sulfanylthiocarbonyl)oxy]pentanedioic acid (HS-C(=S)-O-CH(CO₂H)CH₂CH₂CO₂H)

Scheme XXII

Dimethyl 2-hydroxypentanedioate + BrCH₂CH₂Br →

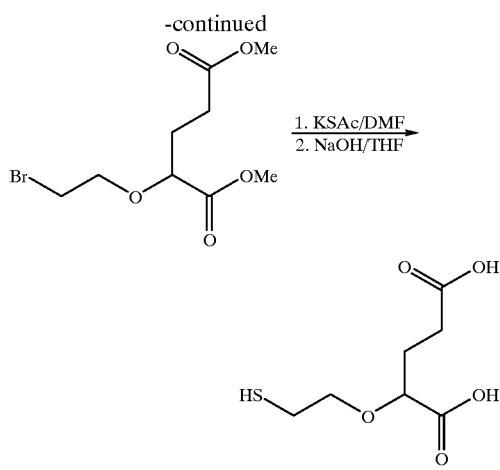

The NAALADase inhibitors of formula II wherein X is a moiety of formula III and A is $(CR_{17}R_{18})_mS$ can be readily prepared via standard synthetic methods such as oxidation of the corresponding thiol.

The compounds of formula II wherein X is a moiety of formula III and A is S can be readily prepared via standard synthetic techniques. For example, Scheme XXII can be modified by starting with an appropriately substituted thio compound. In addition, compounds of this class can also be prepared by Michael addition of an appropriately substituted thiol derivative to an α-, β-unsaturated ester.

The compounds of formula II wherein X is a moiety of formula IV can be readily prepared using standard synthetic pathways, such as reacting a glutamate derivative with carbon disulfide.

ROUTE OF ADMINISTRATION

In the methods of the present invention, the NAALADase inhibitors may be administered by any technique known to be effective in the art including: orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be particularly effective therapeutically as central nervous system targets, the NAALADase inhibitors should preferably readily penetrate the blood-brain barrier when peripherally administered. Compounds which do not readily penetrate the blood-brain barrier can be effectively administered by an intraventricular route.

The NAALADase inhibitors may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the NAALADase inhibitors may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The NAALADase inhibitors may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the NAALADase inhibitors may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The NAALADase inhibitors used in the methods of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

DOSAGE

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

In a preferred embodiment, the NAALADase inhibitors are administered in lyophilized form. In this case, 1 to 100 mg of a NAALADase inhibitor may be lyophilized in individual vials, together with a carrier and a buffer, such as mannitol and sodium phosphate. The compound may be reconstituted in the vials with bacteriostatic water before administration.

The NAALADase inhibitors used in the inventive methods may be administered in combination with one or more therapeutic agents. Specific dose levels for these agents will depend upon considerations such as those identified above.

ADMINISTRATION REGIMEN

For the methods of the present invention, any administration regimen regulating the timing and sequence of drug delivery can be used and repeated as necessary to effect treatment. Such regimen may include pretreatment and/or co-administration with additional therapeutic agents.

COMBINATION WITH OTHER TREATMENTS

In the inventive methods, the NAALADase inhibitors can be co-administered with one or more additional therapeutic agent(s), preferably other anxiolytic agents, memory enhancing agents or agents capable of treating the underlying cause of memory impairment.

Examples of anxiolytic agents which may be combined with the NAALADase inhibitors include without limitation benzodiazepines (chlordiazepoxide, diazepam, clorazepate, flurazepam, halazepam, prazepam, clonazepam, quazepam, alprazolam, lorazepam, oxazepam, temazepam, triazolam); barbiturates; β blockers; and buspirone.

The NAALADase inhibitors can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a NAALADase inhibitor, as well as one or more pharmaceutical excipients, such as wetting, emulsifying and pH buffering agents.

In Vivo Toxicity of NAALADase Inhibitors

The in vivo toxicological effect of NAALADase inhibition has been examined in mice. The results show that NAALADase inhibitors are non-toxic to mice, suggesting that it would be similarly non-toxic to humans when administered at therapeutically effective amounts. Representative disclosure may be found in U.S. Pat. Nos. 5,672,592, 5,795,877, 5,863,536 and 5,880,112, and allowed U.S. patent applications Ser. Nos. 08/825,997, 08/833,628, 08/835,572 and 08/842,360, for which the issue fees have been paid, the entire contents of which patents and applications are herein incorporated by reference.

In Vitro Inhibition of NAALADase Activity

Various compounds used in the inventive methods and pharmaceutical compositions have been tested for in vitro inhibition of NAALADase activity. Some of the results are set forth in U.S. Pat. Nos. 5,672,592, 5,795,877, 5,863,536 and 5,880,112, and allowed U.S. patent applications Ser. Nos. 08/825,997, 08/833,628, 08/835,572 and 08/842,360, the entire contents of which patents and applications are herein incorporated by reference.

Other results are provided below:

IN VITRO INHIBITION OF NAALADASE ACTIVITY

| Compound | $K_i$ (nM) |
| --- | --- |
| 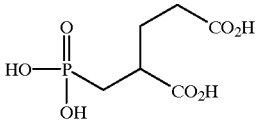 2-(phosphonomethyl)pentanedioic acid | 0.3 |
| 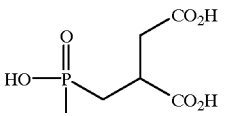 2-(phosphonomethyl)succinic acid | 700 |
| 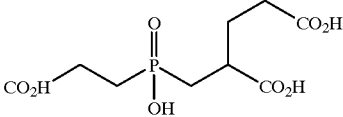 2-[[(2-carboxyethyl)hydroxyphosphinyl]methyl]pentanedioic acid | 2 |
| 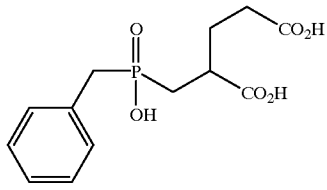 | 53 |
| 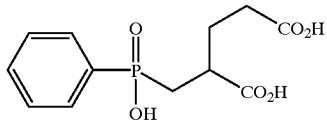 | 36 |
| 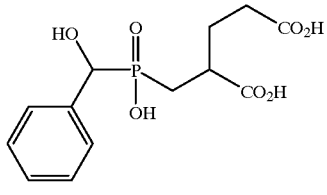 | 54 |
| 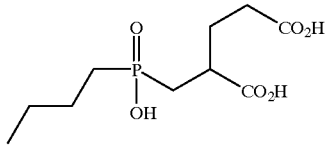 | 114 |

-continued

| Compound | $K_i$ (nM) |
|---|---|
| (3-methylphenyl-P(O)(OH)-CH2-CH(CO2H)-CH2CH2-CO2H) | 180 |
| (PhCH2CH2-P(O)(OH)-CH2-CH(CO2H)-CH2CH2-CO2H) | 148 |
| (PhCH2CH2CH2-P(O)(OH)-CH2-CH(CO2H)-CH2CH2-CO2H) | 232 |
| (4-F-C6H4-P(O)(OH)-CH2-CH(CO2H)-CH2CH2-CO2H) | 532 |
| (CH3-P(O)(OH)-CH2-CH(CO2H)-CH2CH2-CO2H) | 1100 |
| (4-methylbenzyl-P(O)(OH)-CH2-CH(CO2H)-CH2CH2-CO2H) | 68 |
| (3-fluorobenzyl-P(O)(OH)-CH2-CH(CO2H)-CH2CH2-CO2H) | 70 |

-continued

| Compound | $K_i$ (nM) |
|---|---|
| (4-methoxybenzyl-P(O)(OH)-CH2-CH(CO2H)-CH2CH2-CO2H) | 90 |
| (2-fluorobenzyl-P(O)(OH)-CH2-CH(CO2H)-CH2CH2-CO2H) | 145 |
| (pentafluorobenzyl-P(O)(OH)-CH2-CH(CO2H)-CH2CH2-CO2H) | 23 |
| (4-methylphenyl-P(O)(OH)-CH2-CH(CO2H)-CH2CH2-CO2H) | 204 |
| (PhCH2CH2-CH(CH2-P(O)(OH)2)-CH2-CO2H) | 199 |
| ((HO)2P(O)-CH2-CH(CO2H)-CH2CH2-CO2H) | 185 |

-continued

| Compound | $K_i$ (nM) |
|---|---|
| (4-benzyloxybenzyl phosphinate diacid) | 177 |
| (3-trifluoromethylbenzyl phosphinate diacid) | 22 |
| (2-trifluoromethylbenzyl phosphinate diacid) | 92 |
| (4-hydroxybenzyl phosphinate diacid) | 117 |
| (2-methyl-3-phosphonopropanoic acid) | 2 |
| (2-benzyl-3-phosphonopropanoic acid) | 548 |
| (3-phosphonopropanoic acid) | 234 |

-continued

| Compound | $K_i$ (nM) |
|---|---|
| (4-methoxycarbonylbenzyl phosphinate diacid) | 740 |
| (4-carboxybenzyl phosphinate diacid) | 198 |
| (bis tert-butyl diester phosphinate) | 4250 |
| (bis benzyl diester phosphinate) | 13 |
| (phosphinate bis diacid) | 0.6 |

-continued
| Compound | $K_i$ (nM) |
|---|---|
| 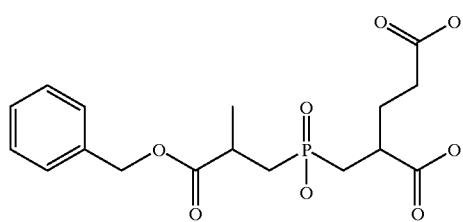 | 95 |
| 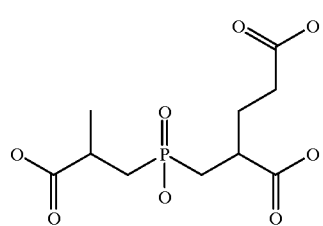 | 2 |
| 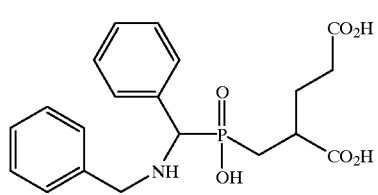 | 313 |
| 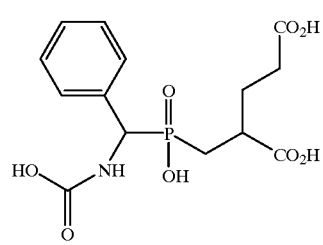 | 2000 |
| 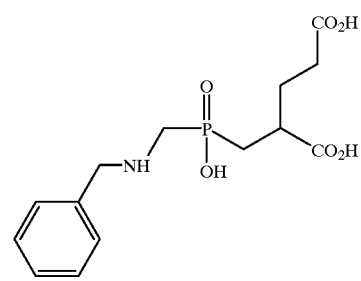 | 52 |
| 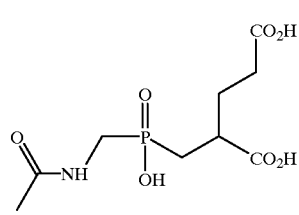 | 118 |
-continued
| Compound | $K_i$ (nM) |
|---|---|
| 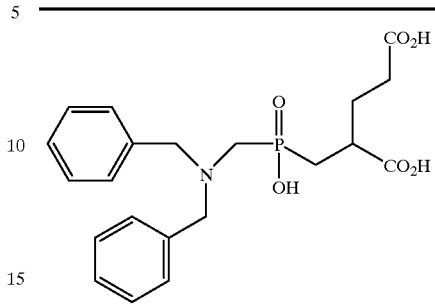 | 175 |
| 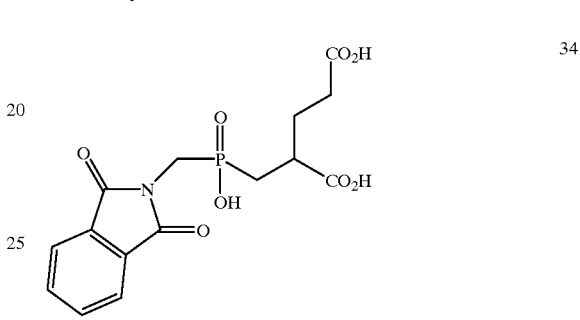 | 34 |
| 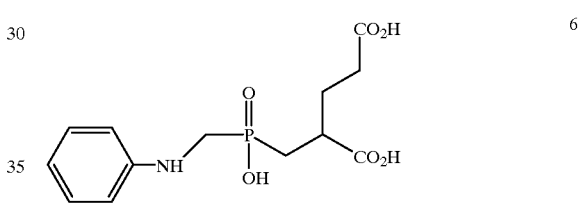 | 6 |
| 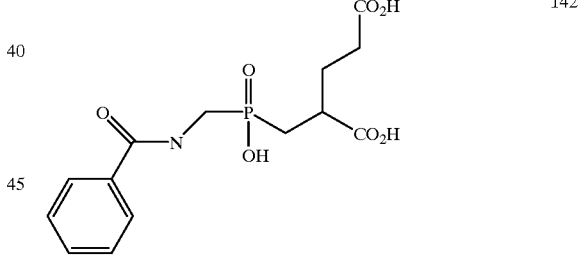 | 142 |
| 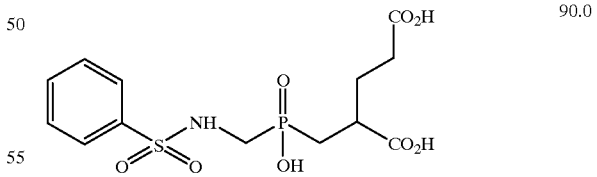 | 90.0 |
| 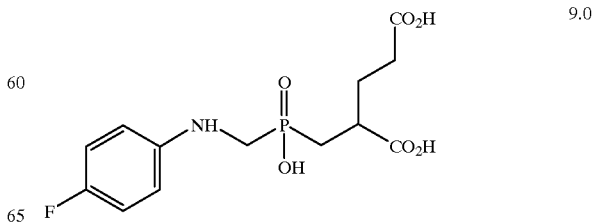 | 9.0 |

-continued

| Compound | $K_i$ (nM) |
|---|---|
| [structure: 4-methoxyphenyl-NH-CH2-P(=O)(OH)-CH2-CH(CO2H)-CH2-CH2-CO2H] | 2 |
| [structure: 4-methylphenyl-NH-CH2-P(=O)(OH)-CH2-CH(CO2H)-CH2-CH2-CO2H] | 5 |
| [structure: 4-tert-butylphenyl-NH-CH2-P(=O)(OH)-CH2-CH(CO2H)-CH2-CH2-CO2H] | 2 |
| [structure: phenyl-NH-C(=S)-NH-CH2-P(=O)(OH)-CH2-CH(CO2H)-CH2-CH2-CO2H] | 75 |
| [structure: HS-CH2-CH2-CH(CO2H)-CH2-CH2-CO2H] 2-(2-sulfanylethyl)pentanedioic acid | 510 |
| [structure: 2-(2-sulfanylhexyl)pentanedioic acid] | 4750 |

-continued

| Compound | $K_i$ (nM) |
|---|---|
| [structure] 2-(1-methyl-2-sulfanylethyl)pentanedioic acid | 843 |
| [structure] 2-(2-sulfanylpropyl)pentanedioic acid | 158 |
| [structure] 2-(2-phenyl-2-sulfanylethyl)pentanedioic acid | 4650 |
| [structure] 2-(1-ethyl-2-sulfanylethyl)pentanedioic acid | 1550 |
| [structure] 2-(2-naphthyl-2-sulfanylethyl)pentanedioic acid | 10000 |

-continued

| Compound | $K_i$ (nM) |
|---|---|
| 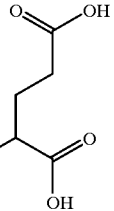<br>2-(3-sulfanylpropyl)pentanedioic acid | 100 |
| 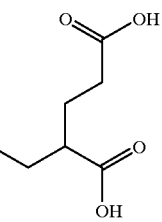<br>2-(3-sulfanyl-2-methylpropyl)pentanedioic acid | 239 |
| 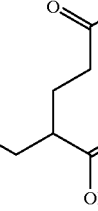<br>2-(4-sulfanylbutyl)pentanedioic acid | 1128 |
| 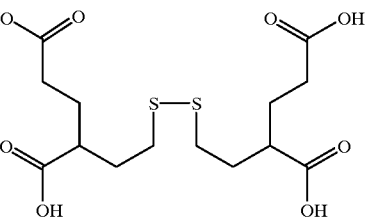<br>2-[2-[(3,5-dicarboxypentyl)dithio]ethyl]pentanedioic acid | 16500 |

EXAMPLES

The following examples are illustrative of the present invention and are not intended to be limitations thereon. Unless otherwise indicated, all percentages are based upon 100% by weight of the final composition.

EXAMPLE 1

Preparation of 2-[[(2,3,4,5,6-pentafluorobenzyl)-hydroxyphosphinyl]methyl]pentanedioic acid Scheme V: $R_1$=2,3,4,5,6-pentafluorobenzyl Hexamethyl-disilazane (21.1 mL, 100 mmol) was added to vigorously stirred ammonium phosphinate (8.30 g, 100 mmol), and the resulting suspension was stirred at 105° C. for 2 hours. A solution of 2,3,4,5,6-pentafluorobenzyl bromide (5.0 g, 27.0 mmol) was then added dropwise to the suspension at 0° C. The mixture was stirred at room temperature for 19 hours. The reaction mixture was then diluted with dichloromethane (50 mL) and washed with 1 N HCl (50 mL). The organic layer was separated, dried over $Na_2SO_4$, and concentrated to give 4.72 g of a white solid. This was dissolved in dichloromethane (50 mL) and benzyl alcohol (3.24 g, 30 mmol) was added to the solution. 1,3-dicyclohexyl-carbodiimide (DCC) (6.19 g, 30 mmol) was then added to the solution at 0° C., and the suspension was stirred at room temperature for 14 hours. The solvent was removed under reduced pressure and the residue was suspended in EtOAc. The resulting suspension was filtered and the filtrate was concentrated. The residue was purified by silica gel chromatography (hexanes: EtOAc, 4:1 to 1:1) to give 2-[[(2,3,4,5,6-pentafluorobenzyl)-hydroxyphosphinyl]-methyl] pentanedioic acid as a white solid (34% yield). Rƒ 0.69 (i-PrOH: $H_2O$, 7:3). $^1$H NMR ($D_2O$) :δ 1.8–2.0 (m, 3H), 2.1–2.3 (m, 1H) 2.3–2.5 (m, 2H), 2.7–2.9 (m, 1H), 3.29 (d, 2H). Elemental Analysis Calculated $C_{13}H_{12}F_5O_6P$, 0.45 $H_2O$:C, 39.20; H, 3.26. Found: C, 39.17; H, 3.28.

EXAMPLE 2

Preparation of 2-(Phosphonomethyl)pentanedioic Acid

Scheme III

Dibenzyl 2-methylenepentanedioate

Benzyl acrylate (500 g, 3.0 mol) was heated in an oil bath to 100° C. Heating was stopped and HMPT (10 g, 61 mmol) was added dropwise while maintaining an internal temperature below 140° C. Once addition was complete, the mixture was stirred and cooled to room temperature. A slurry of silica (5:1 Hexane/EtOAc) was added and the mixture was placed in a column containing a plug of dry silica. The column was washed with 1:1 Hexane/EtOAc and the fractions were combined and evaporated to give 450 g of clear light golden liquid. The liquid was distilled under high vacuum (200 μHg) at 185° C. to give 212 g (4%) of a clear and colorless liquid. $^1$H NMR ($CDCl_3$): 7.3 ppm (m, 10H), 6.2 ppm (s, 1H), 5.6 ppm (s, 1H), 5.2 ppm (s, 2H), 5.1 ppm (s, 2H), 2.6 ppm (m, 4H).

Dibenzyl 2-[[bis(benzyloxy)phosphoryl]methyl]-pentanedioate

Dibenzyl phosphite (9.5 g, 36 mmol) in 350 ml of dichloromethane was cooled to 0° C. To this stirring solution was added trimethyl aluminum (18.2 ml, 2.0 M solution in hexane, 36.4 mmol). After 30 minutes, dibenzyl 2-methylenepentanedioate (2, 6.0 g, 37 mmol) in 90 ml of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100 ml of dichloromethane. The organics were combined, dried ($MgSO_4$), and evaporated to give a clear light golden liquid. The liquid was chromatographed on silica gel (4 cm*30 cm) and eluted with a gradient (4:1–1:1) solvent system (Hexane/EtOAc). The fractions containing the desired product were combined and evaporated to yield dibenzyl 2-[[bis(benzyloxy) phosphorylmethylpentanedioate (7.1 g, 42%) as a clear and colorless liquid. The liquid was then distilled on a Kughleror apparatus at 0.5 mm Hg and 195–200° C. The distillate was discarded and the remaining light golden oil was chromatographed on silica gel (1:1, Hexane/EtOAc) to give 2.9 g of dibenzyl 2-[[bis(benzyloxy)phosphoryl]-methyl]pentanedioate as a clear and colorless oil. TLC Rƒ

0.5 (1:1 Hexane/EtOAc). $^1$H NMR (CDCl$_3$) 7.1–7.4 (m, 20H), 5.05 (s, 2H), 4.8–5.03 (m, 6H), 2.8 (1H), 2.22–2.40 (m, 3H), 1.80–2.02 (m, 3H).

2-(Phosphonomethyl)pentanedioic Acid

The benzyl pentanedioate (2.9 g, 4.9 mmol) was added to a mixture of 20 ml of methanol containing 0.29 g (6 mol %) of 10% Pd/C. This mixture was hydrogenated on a Parr hydrogenator at 40 psi for 24 hours, filtered and evaporated to give a clear slightly golden viscous oil (3, 1.0 g, 90%).

$^1$H-NMR (D$_2$O): 2.6–2.78 (m, H), 2.25–2.40 (m, 2H), 1.75–2.15 (m, 4H).

EXAMPLE 3

Preparation of 2-[[[2-(carboxy)propyl]hydroxyphosphinyl]methyl]pentanedioic acid Scheme X

Di-tert-butyl 2-methylenepentanedioate

Tert-butyl acrylate (465 g, 3.628 mol) was warmed to 100° C. under nitrogen, then hexamethylphosphorous triamide (10 g, 61.2 mmol) was added dropwise and the addition rate was adjusted to maintain the reaction temperature at 100° C. The reaction mixture was allowed to cool, then poured over a plug of silica (~1000 ml) and washed completely off the silica with 4:1 hexane/ethyl acetate. The solvent was removed under reduced pressure and the resulting oil was distilled. Some material was collected from room temperature to 50° C. under high vacuum, and discarded. The temperature was then raised to ~80° C. and the product (300 g, 65%, b.p. 67–70° C. at 300 μ) was collected as a clear oil. $^1$H NMR (CDCl$_3$): δ 1.4 (m, 18H), 2.4 (t, 2H), 2.6 (t, 2H), 5.5 (s, 1H), 6.0 (s, 1H).

Di-tert-butyl 2-[(hydroxyphosphinyl)methyl]pentanedioate

A mixture of ammonium phosphinate (162.6 g, 1.96 mol) and 1,1,1,3,3,3-hexamethyldisilazane (316 g, 1.96 mol) was heated to 105° C. for 2 hours. The reaction mixture was cooled in an ice bath and di-tert-butyl 2-methylenepentane-1,5-dioate (251 g, 0.979 mol) dissolved in dichloromethane (1000 ml) was added dropwise. The reaction mixture was allowed to warm to room temperature overnight. The reaction mixture was then quenched with distilled water (500 ml) and the organic layer was retained. The aqueous layer was washed a second time with dichloromethane and the combined organic layers were dried over magnesium sulfate. Then the solvent was removed under reduced pressure leaving a slightly yellow oil (315 g, 100%) This product was found to be of sufficient purity for use in the next reaction. $^1$H NMR (CDCl$_3$) δ 1.4 (m, 18H), 1.9 (m, 3H), 2.1 (m, 1H), 2.3 (m, 2H), 2.7 (m, 1H), 6.5 & 7.9 (d, 1H, the P-H), 11.0 (s, 1H).

Di-tert-butyl 2-[(tert-butoxyphosphinyl)methyl]pentanedioate

To a solution of di-tert-butyl 2-[(hydroxy-phosphinyl) methyl]pentane-1,5-dioate (315 g, 0.977 mol) in dichloromethane (1000 ml) cooled in an ice bath and under nitrogen were added tert-butanol (123.1 g, 1.66 mol), 4-dimethylaminopyridine (1 g, 8.2 mmol), and 1-ethyl-3-(3-dimethylaminopropyl) carbodiimide (281 g, 1.47 mol). The reaction was allowed to stir overnight. Water was added to the reaction mixture and the dichloromethane layer was retained and dried, and the solvent was removed under reduced pressure. The resulting residue was purified by column chromatography and the desired product was eluted with 1:1 to 2:3 hexane/ethyl acetate. The fractions containing product were concentrated under reduced pressure leaving a clear oil (260 g, 70%). $^1$H NMR (CDCl$_3$) : δ 1.4 (m, 27H), 1.8 (m, 1H), 1.9 (m, 2H), 2.1 (m, 1H), 2.3 (m, 2H), 2.7–2.8 (m, 1H), 6.7 & 8.0 (d, 1H, the P-H).

Di-tert-butyl 2-[[[2-(benzylcarboxy)propyl]tert-butoxyphosphinyl]methyl]pentanedioate To a solution of di-tert-butyl 2-[(tert-butoxy-phosphinyl) methyl]pentane-1,5-dioate (13.62 g, 36.0 mmol) and benzyl methacrylate (6.35 g, 36.0 mmol) in THF (100 ml) under nitrogen was added sodium hydride (0.14 g, 60% dispersion in oil, 3.60 mmol). After three hours, the reaction mixture was poured into water (300 ml) and ether (100 ml) was added. The organic layer was separated and retained, and the aqueous layer was washed again with ether (100 ml). The combined organic extracts were dried over magnesium sulfate and the solvent was removed under reduced pressure. The resulting residue was purified by column chromatography and the product was eluted with 2:3 EtOAc/Hexane. The solvent was removed under reduced pressure leaving a clear oil (10.5 g, 53%). $^1$H NMR (CDCl$_3$): δ 1.3 (m, 3H), 1.5 (m, 27H), 1.7 (m, 2H), 1.9 (m, 2H), 2.2 (m, 4H), 2.6 (m, 1H), 2.9 (m, 1H), 5.1 (m, 2H), 7.3 (m, 5H).

2-[[[2-(Benzylcarboxy)propyl]hydroxyphosphinyl]-methyl]pentanedioic acid

To a solution of di-tert-butyl 2-[[[2-(benzyl-carboxy) propyl]tert-butoxyphosphinyl]methyl]pentane-1,5-dioate (1.6 g, 2.89 mmol) in dichloromethane (10 ml) under nitrogen was added trifluoroacetic acid (10 ml). The reaction mixture was stirred for two hours and then concentrated under reduced pressure. Additional dichloromethane was added to the reaction residue and removed under reduced pressure. The product was dissolved in ethyl acetate and washed with water, then the organic layer was dried over magnesium sulfate and the solvent was removed under reduced pressure leaving a clear oil (800 mg, 72%). $^1$H NMR (D$_2$O): δ 1.2 (m, 3H), 1.6–1.8 (m, 4H), 2.1 (m, 2H), 2.2 (m, 2H), 2.6 (m, 1H), 2.8 (m, 1H), 5.0 (m, 2H), 7.3 (m, 5H). Analysis calculated for C$_{17}$H$_{23}$PO$_8$ 1.0 H$_2$O: C, 50.50; H, 6.23. Found: C, 50.52; H, 5.92.

Di-tert-butyl 2-[[[2-(carboxy)propyl]tert-butoxyphosphinyl]methyl]pentanedioate A solution of di-tert-butyl 2-[[[2-(benzyl-carboxy)propyl] tert-butoxyphosphinyl]methyl]pentane-1,5-dioate (8.9 g, 16.1 mmol), palladium on carbon catalyst (10%, 1.0 g) and ethyl acetate (100 ml) was shaken under hydrogen (60 psi) for 16 hours. The reaction mixture was filtered over celite and the filtrate was concentrated under reduced pressure leaving a clear oil (7.5 g, 100%). $^1$H NMR (CDCl$_3$) δ 1.3 (d, 3H), 1.4–1.5 (m, 27H), 1.8 (m, 2H), 1.9 (m, 2H), 2.2 (m, 4H), 2.7 (m, 1H), 2.9 (m, 1H).

2-[[[2-(Carboxy)propyl]hydroxyphosphinyl]methyl]-pentanedioic acid

To a solution of di-tert-butyl 2-[[[2-(carboxy)-propyl]tert-butoxyphosphinyl]methyl]pentane-1,5-dioate (2.1 g, 4.53 mmol) in dichloromethane (10 ml) under nitrogen was added trifluoroacetic acid (10 ml). The reaction mixture was stirred for two hours and then concentrated under reduced pressure. Additional dichloromethane was added to the reaction residue and removed under reduced pressure. The resulting residue was triturated with acetonitrile, then dried under reduced pressure leaving a thick clear oil (1.2 g, 89%). $^1$H NMR (D$_2$O): δ 1.2 (d, 3H), 1.9 (m, 4H), 2.2 (m, 2H), 2.4 (m, 2H), 2.8 (m, 2H). Analysis calculated for C$_{10}$H$_{17}$PO$_8$ 0.2 CH$_3$CN: C, 41.03; H, 5.83. Found: C, 41.05; H, 5.92.

EXAMPLE 4

Preparation of 2-[({[Benzylamino]methyl} (hydroxy-phosphinyl))methyl]pentanedioic acid
Scheme XI Di-tert-butyl 2-[((tert-butoxy){[benzylamino] methyl}-phosphoryl)methyl]pentane-1,5-dioate A solution of 1,3,5-tribenzylhexahydro-1,3,5-triazine (14.30 g, 40.0 mmol) and di-tert-butyl 2-{[(tert-butoxy) phosphoryl]methyl}pentane-1,5-dioate (37.85 g, 100 mmol) in toluene (200 mL) was stirred at 110° C. for 14 hours. The solvent was removed under reduced pressure and the residual yellow oil was purified by silica gel chromatography (hexanes/ethyl acetate, 2/1) to give 23.40 g of light yellow oil (43% yield): $^1$H NMR (CDCl$_3$) δ 1.40–1.48 (m, 27H), 1.7–2.1 (m, 4H), 2.2–2.4 (m, 3H), 2.6–3.0 (m, 3H), 3.8–4.0 (m, 2H), 7.2–7.4 (m, 5H).

2-[({[Benzylamino]methyl}(hydroxyphosphinyl)) methyl]-pentanedioic acid

To a solution of di-tert-butyl 2-[((tert-butoxy)-{[benzylamino]methyl}phosphoryl)methyl]pentane-1,5-dioate (0.498 g, 1.0 mmol) in dichloromethane (10 mL) was added trifluoroacetic acid (5 mL) at 0° C., and the mixture was stirred at room temperature for eighteen hours. The solvent was removed under reduced pressure. The residual oil was taken up with dichloromethane (10 mL) and concentrated. This process was repeated three times to remove trifluoroacetic acid completely. The resulting oil was crystallized from methanol to give 0.174 g of white solid (53% yield) $^1$H NMR (D$_2$O) δ 1.40–1.48 (m, 27H), 1.7–2.1 (m, 4H), 2.2–2.4 (m, 3H), 2.6–3.0 (m, 3H), 3.8–4.0 (m, 2H), 7.2–7.4 (m, 5H).

EXAMPLE 5

Preparation of 2-[({phenylamino]methyl}(hydroxyphosphinyl))methyl]pentanedioic acid Using a method similar to that described above in Example 4, 2-[({[phenylamino]methyl}(hydroxyphosphinyl))methyl]pentanedioic acid was synthesized: $^1$H NMR (D$_2$O) δ 1.4–1.6 (m, 1H), 1.7–1.9 (m, 3H), 2.2–2.4 (m, 2H), 2.2–2.4 (m, 2H), 2.5–2.7 (m, 1H), 3.53 (d, J=8.8 Hz, 2H), 7.3–7.5 (m, 5H).

EXAMPLE 6

Preparation of 2-[({[4-fluorophenylamino]methyl}-(hydroxyphosphinyl))methyl]pentanedioic acid Using a method similar to that described above in Example 4, 2- [({[4-fluorophenylamine]methyl}(hydroxyphosphinyl))methyl]pentanedioic acid was synthesized: $^1$H NMR (D$_2$O) δ 1.5–1.7 (m, 1H) 1.8–2.0 (m, 3H), 2.3–2.5 (m, 2H), 2.6–2.7 (m, 1H), 3.84 (d, J=9.0 Hz, 2H), 7.2–7.5 (4H).

EXAMPLE 7

Preparation of 2-[({[4-methoxyphenylamino] methyl}-(hydroxyphosphinyl))methyl]pentanedioic acid Using a method similar to that described above in Example 4, 2-[({[4-Methoxyphenylamino]methyl}-(hydroxyphosphinyl))methyl]pentanedioic acid was synthesized: $^1$H NMR (D$_2$O) δ 1.2–1.3 (m, 1H), 1.6–1.7 (m, 3H), 2.22–2.23 (m, 2H), 2.3–2.5 (m, 1H), 3.4 (d, J=8.9 Hz, 2H), 3.7 (s, 3H), 7.0 (d, J=12 Hz, 2H) 7.4 (d, J=12 Hz, 2H).

EXAMPLE 8

Preparation of 2-({[phenylsulfonamido)methyl]-(hydroxyphosphinyl)}methyl)pentanedioic acid Using a method similar to that described above in Example 4, 2-({(phenylsulfonamido)methyl](hydroxyphosphinyl)}methyl)pentanedioic acid was synthesized: $^1$H NMR (D$_2$O) δ 1.6–2.1 (m, 4H), 2.3–2.4 (m, 2H), 2.5–2.7 (m, 1H), 2.9–3.1 (m, 3H), 7.7–8.0 (m, 5H).

EXAMPLE 9

Preparation of 2-({[(phenylcarboxamido)methyl]-(hydroxyphosphinyl)}methyl)pentanedioic acid
Scheme XII Di-tert-butyl 2-{[(aminomethyl) (tert-butoxy)-phosphoryl]methyl}pentane-1,5-dioate To a solution of di-tert-butyl 2-[( (tert-butoxy)-{[benzylamino]methyl}phosphoryl)methyl]pentane-1,5-dioate (8.20 g, 16.5 mmol) in ethanol (100 mL) was added palladium on carbon (0.50 g), and the suspension was shaken under hydrogen (50 psi) for 4 days. The catalyst was removed by filtration through a pad of Celite. The filtrate was concentrated to give 6.629 g of colorless oil (99% yield): $^1$H NMR (CD$_3$OD) δ 1.40–1.60 (m, 27H), 1.80–2.00 (m, 3H), 2.2–2.4 (m, 3H), 2.7–3.0 (m, 3H).

Di-tert-butyl 2 -({(tert-butoxy) [(phenylcarboxamido)-methyl]phosphoryl}methyl) pentane-1,5-dioate To a solution of di-tert-butyl 2-{[(aminomethyl)-(tert-butoxy)phosphoryl]methyl}pentane-1,5-dioate (1.222 g, 3.0 mmol) and benzoyl chloride (0.46 mL, 4.0 mmol) in dichloromethane (10 mL) was added triethylamine (0.56 mL, 4.0 mmol) at 0° C., and the mixture was stirred at room temperature for 16 hours. The reaction mixture was diluted with dichloromethane (15 mL), washed with 1 N HCl (25 mL), dried over Na$_2$SO$_4$, and concentrated. The crude material was purified by silica gel chromatography (ethyl acetate/hexanes 2/1) to give 1.259 g of colorless oil (74% yield) $^1$H NMR (CDCl$_3$) δ 1.30–1.60 (m, 27H), 1.60–2.00 (m, 3H), 2.20–2.40 (m, 3H), 2.70–2.90 (m, 3H), 3.5–4.2 (m, 2H), 7.0–7.3 (m, 1H), 7.4–7.6 (m, 3H), 7.8–7.9 (m, 1H).

2-({[(Phenylcarboxamido)methyl] (hydroxyphosphinyl)}-methyl)pentanedioic acid

To a solution of di-tert-butyl 2-({(tert-butoxy)-[(phenylcarboxamido}methyl]phosphoryl methyl)pentane-1,5-dioate (1.230 g, 2.4 mmol) in dichloromethane (10 mL) was added trifluoroacetic acid (5 mL) at room temperature, and the mixture was stirred at room temperature for 18 hours. The solvent was removed under reduced pressure. The residual oil was taken up with dichloromethane (10 mL) and concentrated. This process was repeated three times to remove trifluoroacetic acid completely. The resulting oil was crystallized from acetonitrile-water to give 0.620 g of white solid (75% yield): $^1$H NMR (D$_2$O) δ 1.9–2.1 (m, 3H), 2.2–2.4 (m, 1H), 2.4–2.6 (m, 2H), 2.8–3.0 (m, 1H), 3.7–3.9 (m, 2H), 7.5–7.9 (m, 5H).

EXAMPLE 10

Preparation of 2-(2-sulfanylethyl)pentanedioic acid
Scheme XIII, $R_{10}$=hydrogen 3-(2-Oxotetrahydro-3-thiophenyl)propanoate

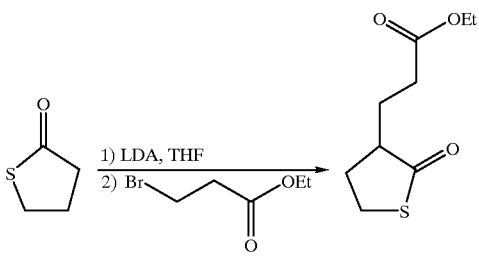

To a cooled solution (−78° C.) of lithium diisopropylamide (LDA) (98 mmol) in THF (100 ml) was added dropwise γ-thiobutyrolactone (10 g, 98 mmol). After stirring for fifteen minutes, ethyl 3-bromopropanoate (35.4 g, 196 mmol) was added and the reaction allowed to warm to room temperature overnight. The solvent was removed under reduced pressure and the resulting residue was purified by column chromatography yielding 3 g (16%) of clear oil. $^1$H NMR (CDCl$_3$) δ 1.2 (t, 3H), 1.7 (m, 1H), 1.9 (m, 1H), 2.1 (m, 1H), 2.4 (t, 2H), 2.5 (m, 2H), 3.3 (t, 2H), 4.2 (q, 2H).

2-(2-sulfanylethyl)pentanedioic acid

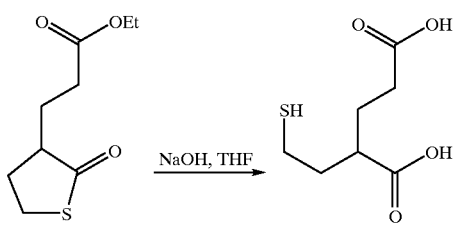

To a solution of ethyl 3-(2-oxotetrahydro-3-thiophenyl) propanoate (0.77 g, 3.81 mmol) in THF (5 ml) was added sodium hydroxide (1 M in water, 5 ml). The mixture was allowed to stir for two days, then the THF was removed under reduced pressure, the aqueous layer was washed with ether, then acidified to pH 1 with HCl and extracted with ethyl acetate. The combined ethyl acetate extracts were dried over magnesium sulfate and the solvent was removed under reduced pressure. The resulting residue was purified by column chromatography yielding a 150 mg of clear oil (20%). $^1$H NMR (d6-DMSO) δ 1.7 (m, 3H), 1.8 (m, 1H), 2.2 (m, 2H), 2.3–2.5 (m, 4H). Analysis calculated for $C_7H_{12}SO_4$: C, 43.74; H, 6.29; S, 16.68. Found: C, 43.61; H, 6.39; S, 16.55.

EXAMPLE 11

Preparation of 2-(3-sulfanylpropyl)Pentanedioic acid
Scheme XIX 2,2-dimethyl-5-[3-[(triphenylmethyl)thio]propyl]-1,3-dioxane-4,6-dione (I)

20 mmol of 3-[(triphenylmethyl)thio]propionic acid (6.9 g) was dissolved with 22 mmol Meldrum's acid (2,2-dimethyl-1,3-dioxane-4,6-dione) (3.2 g) and 31 mmol 4-dimethylaminopyridine (3.85 g) in 100 ml CH$_2$Cl$_2$. The reaction mixture was cooled to −5° C. and a solution of 22 mmol of dicyclohexyl carbodiimide (4.74 g) in 50 ml CH$_2$Cl$_2$ was added dropwise over 1 hour. The mixture was left at <0° C. temperature overnight, during which time tiny crystals of dicyclohexylurea precipitated. After filtration, the reaction mixture was washed 4× with 10% KHSO$_4$, 1× with brine and dried with MgSO$_4$ for 2 hours. This solution was used for the second step without characterization or further purification.

The solution from the previous reaction was cooled to −5° C. and 13.3 ml (220 mmol) of 98% acetic acid was added. Then 1.85 g (50 mmol) of NaBH$_4$, was added in small portions while stirring over 1 hour. The reaction mixture was left in the refrigerator overnight and then washed 3× with water and 2× with brine. Organic phase was dried with MgSO$_4$, filtered and evaporated to dryness. The residue was dissolved in EtOAc, the precipitated small amount of dicyclohexylurea was filtered off and filtrate was brought to crystallization by addition of hexane. Yield 7.5 g of 2,2-dimethyl-5-[3-[(triphenylmethyl)-thio]propyl]-1,3-dioxane-4,6-dione (I) (86%—two steps). $_{13}$C-NMR δ 20.0(q), 26.2 (q), 27.2(t), 28.9(t), 32.0(t), 46.2(d), 67.0(s), 105.3(s), 127.0 (d), 128.3(d), 130.0(d), 145.2(s), 165.6(s).

2,2-Dimethyl-4,6-dioxo-5-[3-[(triphenylmethyl) thio]-propyl]-1,3-dioxane-5-propanoic acid methylester (II)

5 mmol of 2,2-dimethyl-5-[3-[(triphenylmethyl)-thio]-propyl]-1,3-dioxane-5-propanoic-4,6-dione (I) (2.3 g), was dissolved with 20 mmol methyl-3-bromopropionate (3.34g= 2.18 ml) and 4.6 ml of 4.37 M methanolic solution of sodium methoxide (20 mmol) in 10 ml of methanol. The reaction mixture was heated to 60° C. overnight after which TLC in hexane/ethylacetate 1:1 detected no starting material. The mixture was then evaporated to dryness and mixed with 40 ml of aqueous 10% KHSO$_4$. The organic material was extracted by 3 portions of EtOAc, the organic layers were combined dried with MgSO$_4$ and evaporated. The residue was crystallized from hexane/ethylacetate to yield 2.1 g (77%) of 2,2-dimethyl-4,6-dioxo-5-[3-[(triphenyl-methyl)thio]propyl]-1,3-dioxane-5-propanoic acid methyl ester (II), $^{13}$C-NMR (CDCl$_3$) δ 24.6, 29.4, 29.5, 29.6, 31.4, 32.6, 37.7, 51.9, 52.8, 66.8, 105.7, 126.7, 127.9, 129.5, 144.7, 168.4, 172.0.

6-[(triphenylmethyl)thio]-1,3,3-hexanetricarboxylic acid (III)

2.56 mmol of 2,2-dimethyl-4,6-dioxo-5-[3-[(triphenylmethyl)thio]propyl]-1,3-dioxane-5-propanoic acid methyl ester (II) (1.4 g) with 18 mmol of sodium hydroxide (0.72 g) was dissolved in a mixture of 5 ml of 1,4-dioxane and 5 ml of water. The mixture was then heated to 100° C. for 1 hour, evaporated to dryness, dissolved in water and precipitated by addition of 1 M sulfuric acid. The precipitate was filtered off, washed with water and dried in a dessicator. Yield 1.36 g of 6-[(triphenylmethyl)-thio]-1,3, 3-hexanetricarboxylic acid (III) (−100%), $^{13}$C-NMR (MeOH) δ 25.4, 29.2, 30.7, 33.5, 33.7, 58.0, 68.3, 128.1, 129.3, 131.2, 146.7, 174.9, 176.9.

6-[(triphenylmethyl)thio]-1,3-hexanedicarboxylic acid (IV)

2.56 mmol of 6-[(triphenylmethyl)thio]-1,3,3,-hexanetricarboxylic acid (III) (1.36 g) was dissolved in 5 ml of dimethylsulfoxide and the solution was heated to 100° C. for 1 hour, evaporated to dryness, dissolved in water and precipitated by addition of 1 M sulfuric acid. The precipitated oil solidified after 1 hour treatment in an ultrasound bath. The solid was filtered off, washed with water and dried in a dessicator. Yield 1.1 g of 6-[(triphenylmethyl)-thio]-1,3-hexanedicarboxylic acid (IV) (89% two steps from II), $^{13}$C-NMR (MeOH) $\delta$ 27.9, 28.6, 33.0 (two carbons), 33.1, 45.9, 68.1, 128.1, 129.2, 131.2, 146.8, 177.1, 179.4.

2-(3-sulfanylpropyl)pentanedioic acid (V)

2.46 mmol of 6-[(triphenylmethyl)thio]-1,3-hexanedicarboxylic acid (IV) (1.1 g) with 5 mmol triisopropylsilane (0.79 g) was dissolved in a mixture of 3 ml $CH_2Cl_2$/3 ml trifluoroacetic acid and left to stand at room temperature for 1 hour. The mixture was then evaporated to dryness and washed 3× with hexane. The remaining oily residue was dissolved in water, filtered and lyophilized to yield 0.35 g of 2-(3-sulfanylpropyl)pentanedioic acid (V) (76%), $^{13}$C-NMR (MeOH) $\delta$ 25.2(t), 28.8(t), 32.4(t), 33.0(t), 33.2(t), 45.9(d), 177.2(s), 179.6(s).

EXAMPLE 12

Preparation of 2-(4-sulfanylbutyl)pentanedioic acid 2-(4-sulfanylbutyl)pentanedioic acid was prepared using the methods described above for 2-(3-sulfanylpropyl) pentanedioic acid. $^{13}$C-NMR (MeOH) $\delta$ 25.1(t), 27.4(t), 28.8(t), 33.0(t), 33.2(t), 35.4(t), 46.3(d), 177.2(s), 179.7(s).

EXAMPLE 13

Preparation of 2-(3-sulfanyl-2-methylpropyl)-pentanedioic acid 2-(3-sulfanyl-2-methylpropyl)pentanedioic acid (mixture of two diastereoisomers) was prepared using the methods described above for 2-(3-sulfanylpropyl)-pentanedioic acid. $^{13}$C-NMR (MeOH) $\delta$ 18.9(q), 19.5(q), 29.1(t), 29.6(t), 31.7 (t), 32.6(t), 32.9(t), 33.0(t), 35.5(d), 35.9(d), 39.2(t), 39.7(t), 44.2(d), 44.3(d), 177.0(s), 177.1(s), 179.7(s), 179.9(s).

EXAMPLE 14

Anxiolytic Activity

Compounds 1, 2 and 3 (identified under "DEFINITIONS") were tested in an anxiolytic model termed "passive avoidance". Compounds 1, 2 and 3 were found to exhibit anxiolytic properties. In fact, in some experiments they performed better than the known anxiolytic agent, flurazepam. The results of this study are set forth in TABLES I and II of the APPENDIX.

The passive avoidance test consists of an acquisition and a retention trial. On the day prior to dosing, the animal is placed into the shuttlebox and allowed to acclimate. A conditioned stimulus (light) is presented for approximately 100 seconds. When the animal crosses to the dark compartment, a mild (0.5 mA) footshock is presented until the animal returns to the lighted compartment or for approximately 10 seconds. Animals failing to cross during acquisition trial is randomly replaced. The day following acquisition, animals are administered test article, saline or flurazepam 10 minutes prior to being placed in the shuttlebox and tested for retention as described above. Latency to cross (in seconds) is recorded.

EXAMPLE 15

Anxiolytic Activity 2-(2-sulfanylpropyl)pentanedioic acid and 2-(3-sulfanylpropyl)pentanedioic acid are tested in the passive avoidance anxiolytic model. Each of the compounds is found to exhibit anxiolytic properties.

EXAMPLE 16

Memory Enhancing Activity

The effects of NAALADase inhibitors on memory enhancement are tested on a T16 maze model. The T16 maze model is described in detail elsewhere (see, for example, Shimada et al., *European Journal of Pharmacology*, Vol. 263, pp. 293–300 (1994); Spangler, *Physiology & Behavior*, Vol. 56, No. 1, pp. 95–101 (1994)).

Pretraining is conducted in a 2-meter long straight runway, constructed of clear Plexiglass. The floor is constructed of stainless steel grids wired to distribute a constant-current scrambled shock. A hand-held switch initiates a foot-shock and starts a clock that recorded the time to traverse the runway. Interchangeable black Plexiglas start and goal boxes can be placed over the grid floors at either end of the runway. On the day of pretraining, the rat is placed in one of the black boxes, the box is inserted into the start position of the runway, and a timer is initiated. The rat is pushed gently into the runway and is allowed 10 seconds to enter the goalbox to avoid a footshock (0.8 mA). Upon entry to the goal box, a guillotine door is lowered, the goal box is returned to the start area (after a 90 second ITI), and the next trial is initiated. Each rat continues to receive massed training trials until a criterion of 13/15 avoidances is met (max=30 trials).

Acquisition training is conducted in a clear Plexiglas 14-unit T-maze. The maze is separated into five distinct sections by guillotine doors that prevent animals from backtracking into previous sections. Nonfunctional guillotine doors at the entry to each cul-de-sac prevent the functional doors from being used as cues to the correct pathway. A switchbox triggers a clock which, when timed out, activates a counter that record the number of shocks (max=5/trial). Infrared photocells throughout the maze record the number of errors (defined as any deviation from the correct pathway) and runtime. The maze is surrounded by painted gray wooden walls to reduce extra-maze visual cues. Speakers are located under the maze at each corner and provide music to reduce auditory cues. The maze can be hoisted by motor driven pulleys to clean the grid floor and reduce the presence of odor cues.

For acquisition training, 24 hours after pretraining, the rat is placed into a start box and the box is inserted into the start position. The rat is pushed gently into the maze, the door is closed, and the clock controlling the shock contingency is initiated. In each section of the maze, the rat is given 10 seconds to escape through the door to the next section. After 10 seconds, a footshock is delivered until the rat escapes through the door. When the rat passes into the next section, the door is lowered behind the animal, and the clock contingency is reset. Upon entering the goal box, the door is closed, the box is placed in a holding area for 90 seconds, and the maze is hoisted for cleaning. Each rat receives a total of 15 massed trials with a 2 minute interial interview.

Rats are randomly assigned to treatment groups. Saline and NAALADase inhibitors, including Compounds 1, 2 and 3, 2-(2-sulfanylpropyl)-pentanedioic acid and 2-(3-sulfanylpropyl)pentanedioic acid are administered by intraperitoneal injection approximately 30 minutes prior to initiation of testing. Doses are chosen to be within the therapeutically effective range for each compound.

Rats treated with a therapeutically effective amount of a NAALADase inhibitor perform better than control rats treated with saline. The results demonstrate that NAALA-Dase inhibitors enhance memory in mammals.

All publications, patents and patent applications identified above are herein incorporated by reference.

The invention being thus described, it will be obvious that the same may be varied in many ways. Such variations are not to be regarded as a departure from the spirit and scope of the invention and all such modifications are intended to be included within the scope of the following claims.

APPENDIX

TABLE I

Passive Avoidance-Individual Animals

| Treatment | Animal # | Latency to Cross (seconds) Acquisition Trial | Latency to Cross (seconds) Retention Trial |
|---|---|---|---|
| Saline 0 mg/kg; Ip | 16 | 9.7 | 73.2 |
| | 2 | 9.0 | 16.1 |
| | 3 | 4.1 | 2.9 |
| | 4 | 3.3 | 1.5 |
| | 5 | 0.2 | 8.9 |
| | 6 | 1.3 | 27.9 |
| | 7 | 4.9 | 11.0 |
| | 8 | 16.4 | 5.3 |
| | 9 | 6.9 | 27.4 |
| | 10 | 14.2 | 100.0 |
| | 11 | 16.8 | 2.5 |
| | 12 | 12.5 | 100.0 |
| | 13 | 1.2 | 21.3 |
| | 14 | 2.1 | 7.0 |
| | 15 | 5.2 | 7.6 |
| | MEAN | 7.2 | 27.5 |
| | SD | 5.6 | 34.4 |
| Flurazepam 3 mg/kg; Ip | 1 | 7.0 | 83.3 |
| | 17 | 9.5 | 100.0 |
| | 18 | 8.8 | 100.0 |
| | 19 | 2.8 | 5.5 |
| | 20 | 19.3 | 100.0 |
| | 21 | 5.4 | 4.7 |
| | 22 | 8.2 | 100.0 |
| | 23 | 28.2 | 16.1 |
| | 24 | 7.1 | 65.3 |
| | 25 | 2.4 | 6.9 |
| | 26 | 16.7 | 2.1 |
| | 27 | 8.4 | 34.1 |
| | 28 | 11.3 | 2.2 |
| | 29 | 6.9 | 47.5 |
| | 30 | 9.1 | 34.9 |
| | MEAN | 10.1 | 47.5 |
| | SD | 6.7 | 40.1 |
| Compound 2 100 mg/kg; Ip | 31 | 4.0 | 9.8 |
| | 32 | 0.1 | 7.1 |
| | 33 | 14.9 | 4.8 |
| | 34 | 5.0 | 100.0 |
| | 35 | 6.4 | 100.0 |
| | 36 | 9.5 | 88.4 |
| | 37 | 4.6 | 7.8 |
| | 38 | 5.7 | 15.8 |
| | 39 | 0.1 | 100.0 |
| | 40 | 13.0 | 100.0 |
| | 41 | 5.1 | 100.0 |
| | 42 | 6.2 | 100.0 |
| | 43 | 10.1 | 68.4 |
| | 44 | 4.3 | 100.0 |
| | 45 | 11.4 | 100.0 |
| | MEAN | 6.7 | 66.8[a] |
| | SD | 4.3 | 43.1 |

TABLE I-continued

Passive Avoidance-Individual Animals

| Treatment | Animal # | Latency to Cross (seconds) Acquisition Trial | Latency to Cross (seconds) Retention Trial |
|---|---|---|---|
| Saline 0 mg/kg; Ip | 104 | 10.3 | 14.9 |
| | 107 | 13.1 | 1.0 |
| | 110 | 1.8 | 17.5 |
| | 113 | 8.8 | 11.8 |
| | 115 | 0.3 | 12.0 |
| | 201 | 2.7 | 13.4 |
| | 204 | 1.0 | 0.4 |
| | 206 | 12.0 | 6.4 |
| | 214 | 2.5 | 16.1 |
| | 215 | 0.6 | 2.1 |
| | 305 | 9.5 | 17.5 |
| | 401 | 6.8 | 49.2 |
| | 402 | 11.6 | 18.7 |
| | 411 | 5.5 | 3.1 |
| | 413 | 43.6 | 21.1 |
| | MEAN | 8.7 | 13.7 |
| | SD | 10.7 | 12.0 |
| Flurazepam 5 mg/kg; Ip | 101 | 6.6 | 11.2 |
| | 102 | 39.8 | 56.3 |
| | 108 | 2.7 | 10.5 |
| | 109 | 10.6 | 23.9 |
| | 111 | 0.5 | 6.5 |
| | 112 | 0.1 | 6.0 |
| | 203 | 7.4 | 13.4 |
| | 207 | 4.0 | 0.8 |
| | 208 | 4.9 | 21.4 |
| | 212 | 14.7 | 2.9 |
| | 306 | 10.1 | 67.2 |
| | 307 | 9.5 | 19.0 |
| | 310 | 1.9 | 58.3 |
| | 404 | 12.9 | 4.8 |
| | 407 | 0.7 | 9.7 |
| | MEAN | 8.4 | 20.8 |
| | SD | 9.8 | 21.7 |
| Compound 3 100 mg/kg; Ip | 105 | 9.3 | 6.6 |
| | 202 | 0.2 | 33.0 |
| | 205 | 2.0 | 89.8 |
| | 308 | 5.9 | 100.0 |
| | 309 | 6.1 | 5.2 |
| | 312 | 25.0 | 5.9 |
| | 313 | 2.2 | 100.0 |
| | 314 | 10.5 | 8.5 |
| | 403 | 11.8 | 100.0 |
| | 405 | 11.5 | 100.0 |
| | 408 | 9.2 | 4.6 |
| | 409 | 0.8 | 9.9 |
| | 410 | 0.6 | 47.4 |
| | 412 | 2.9 | 12.9 |
| | 415 | 18.6 | 20.6 |
| | MEAN | 7.8 | 43.0 |
| | SD | 7.1 | 41.9 |
| Compound 2 100 mg/kg; Ip | 103 | 0.0 | 3.1 |
| | 106 | 11.4 | 33.9 |
| | 114 | 12.1 | 100.0 |
| | 209 | 1.5 | 13.2 |
| | 210 | 1.6 | 6.6 |
| | 211 | 7.0 | 39.4 |
| | 213 | 6.8 | 7.9 |
| | 301 | 20.0 | 33.2 |
| | 302 | 2.3 | 100.0 |
| | 303 | 0.6 | 8.4 |
| | 304 | 9.6 | 41.5 |
| | 311 | 3.2 | 19.5 |
| | 315 | 10.4 | 7.3 |
| | 406 | 5.7 | 100.0[b] |
| | 414 | 18.7 | 0.3 |
| | MEAN | 7.5 | 29.6 |
| | SD | 6.5 | 32.9 |

[a]Indicates significance difference compared to Group 1; $p \leq 0.05$.
[b]Omitted from statistical analysis; animal showing clinical signs prior to dosing.

TABLE II

Passive Avoidance-Individual Animals

| Treatment | Animal # | Latency to Cross (seconds) |
|---|---|---|
| Control PO | 216 | 17.9 |
| | 217 | 100.0 |
| | 218 | 2.3 |
| | 219 | 5.8 |
| | 220 | 100.0 |
| | 221 | 11.8 |
| | 222 | 17.2 |
| | 223 | 45.7 |
| | 224 | 26.9 |
| | 225 | 75.3 |
| | 226 | 10.3 |
| | 227 | 100.0 |
| | 228 | 8.7 |
| | 229 | 40.3 |
| | 230 | 100.0 |
| | Mean | 44.1 |
| | SEM | 10.2 |
| Flurazepam, 5 mg/kg IP | 103 | 4.7 |
| | 104 | 9.6 |
| | 105 | 4.1 |
| | 106 | 26.0 |
| | 107 | 0.3 |
| | 108 | 4.0 |
| | 109 | 8.0 |
| | 110 | 3.5 |
| | 111 | 12.0 |
| | 112 | 4.0 |
| | 113 | 16.9 |
| | 114 | 89.0 |
| | 115 | 6.4 |
| | 131 | 4.1 |
| | 132 | 0.3 |
| | Mean | 12.9 |
| | SEM | 5.7 |
| Compound 1 1 mg/kg PO | 316 | 5.9 |
| | 317 | 15.8 |
| | 318 | 28.4 |
| | 319 | 30.3 |
| | 320 | 100.0 |
| | 321 | 12.3 |
| | 322 | 27.9 |
| | 323 | 23.5 |
| | 324 | 3.9 |
| | 325 | 13.1 |
| | 326 | 100.0 |
| | 327 | 0.2 |
| | 328 | 41.3 |
| | 329 | 100.0 |
| | 330 | 20.1 |
| | Mean | 34.8 |
| | SEM | 9.1 |
| Compound 1 10 mg/kg PO | 416 | 1.8 |
| | 417 | 28.5 |
| | 418 | 64.1 |
| | 419 | 3.2 |
| | 420 | 14.7 |
| | 421 | 10.3 |
| | 422 | 3.3 |
| | 423 | 24.6 |
| | 424 | 9.4 |
| | 425 | 100.0 |
| | 426 | 22.7 |
| | 427 | 6.6 |
| | 428 | 14.0 |
| | 429 | 38.8 |
| | 430 | 12.1 |
| | Mean | 23.6 |
| | SEM | 6.9 |

TABLE II-continued

Passive Avoidance-Individual Animals

| Treatment | Animal # | Latency to Cross (seconds) |
|---|---|---|
| Compound 1 10 mg/kg PO | 416 | 1.8 |
| | 417 | 28.5 |
| | 418 | 64.1 |
| | 419 | 3.2 |
| | 420 | 14.7 |
| | 421 | 10.3 |
| | 422 | 3.3 |
| | 423 | 24.6 |
| | 424 | 9.4 |
| | 425 | 100.0 |
| | 426 | 22.7 |
| | 427 | 6.6 |
| | 428 | 14.0 |
| | 429 | 38.8 |
| | 430 | 12.1 |
| | Mean | 23.6 |
| | SEM | 6.9 |
| Compound 1 100 mg/kg PO | 516 | 15.0 |
| | 517 | 19.2 |
| | 518 | 5.6 |
| | 519 | 19.3 |
| | 520 | 6.2 |
| | 521 | 55.7 |
| | 522 | 25.5 |
| | 523 | 21.5 |
| | 524 | 6.6 |
| | 525 | 15.1 |
| | 526 | 8.4 |
| | 527 | 17.4 |
| | 528 | 0.5 |
| | 529 | 0.7 |
| | 530 | 52.8 |
| | Mean | 18.0 |
| | SEM | 4.3 |

What is claimed is:

1. A method of treating a glutamate mediated disease, disorder, or condition selected from the group consisting of anxiety, anxiety disorder, and memory impairment in a mammal in need thereof, comprising administering to said mammal an effective amount of a NAALADase inhibitor, wherein said NAALADase inhibitor is a compound of formula II.

2. The method of claim 1, wherein the NAALADase inhibitor is a compound of formula VI

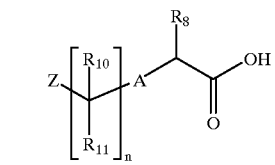

VI or a pharmaceutically acceptable equivalent, wherein:
n is 0, 1, 2 or 3;
Z is SH, $SO_3R_{13}$, $SO_2R_{13}$, $SOR_{13}$ or S $(NR_{13}R_{14})_2R_{15}$; and
A is O, S or $CR_{17}R_{18}$.

3. The method of claim 2, wherein Z is SH.
4. The method of claim 3, wherein $R_8$ is —$(CH_2)_2COOH$.
5. The method of claim 3, wherein the compound of formula VI is selected from the group consisting of:
2-(2-sulfanylethyl)pentanedioic acid;
3-(2-sulfanylethyl)-1,3,5-pentanetricarboxylic acid;
2-(2-sulfanylpropyl)pentanedioic acid;

2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

6. The method of claim 5, wherein the compound of formula VI is selected from the group consisting of 2-(2-sulfanylethyl)pentanedioic acid, sulfanylpropyl) pentanedioic acid, 2-(3-sulfanylpropyl) pentanedioic acid and pharmaceutically acceptable equivalents.

7. The method of claim 6, wherein the compound of formula VI is an enantiomer or an enantiomer-enriched mixture.

8. The method of claim 1, wherein the NAALADase inhibitor is administered in combination with at least one additional therapeutic agent.

9. The method of claim 1, wherein the glutamate mediated disease, disorder or condition is an anxiety disorder selected from the group consisting of panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS.

10. The method of claim 1, wherein the glutamate mediated disease, disorder or condition is memory impairment.

* * * * *

UNITED STATES PATENT AND TRADEMARK OFFICE
CERTIFICATE OF CORRECTION

PATENT NO. : 6,228,888 B1
DATED : May 8, 2001
INVENTOR(S) : Barbara S. Slusher

It is certified that error appears in the above-identified patent and that said Letters Patent is hereby corrected as shown below:

Column 52,
Line 43, after "formula II" insert the following:

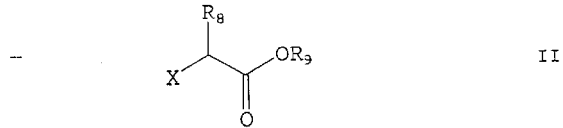

or a pharmaceutically acceptable equivalent, wherein:
    X is a moiety of formula III, IV or V

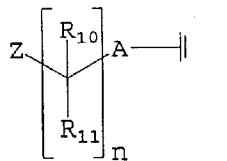            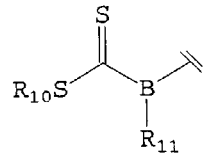

III                      IV

PATENT NO. : 6,228,888 B1
DATED : May 8, 2001
INVENTOR(S) : Barbara S. Slusher

It is certified that error appears in the above-identified patent and that said Letters Patent is hereby corrected as shown below:

(continued)

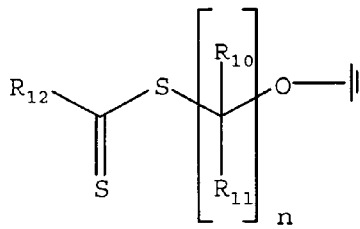

V;

m and n are independently 0, 1, 2, 3 or 4;
Z is $SR_{13}$, $SO_3R_{13}$, $SO_2R_{13}$, $SOR_{13}$, $SO(NR_{13})R_{14}$ or $S(NR_{13}R_{14})_2R_{15}$;
B is N or $CR_{16}$;
A is O, S, $CR_{17}R_{18}$ or $(CR_{17}R_{18})_mS$;
$R_9$ and $R_{13}$ are hydrogen;
$R_8$, $R_{10}$, $R_{11}$, $R_{12}$, $R_{14}$, $R_{15}$, $R_{16}$, $R_{17}$ and $R_{18}$ are independently hydrogen, $C_1$-$C_9$ straight or branched chain alkyl, $C_2$-$C_9$ straight or branched chain alkenyl, $C_3$-$C_8$ cycloalkyl, $C_5$-$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and
$Ar_1$ is a carbocyclic or heterocyclic moiety, which is unsubstituted or substituted with one or more substituent(s);
provided that when X is a moiety of formula III and A is O, then n is 2, 3 or 4; when X is a moiety of formula III and A is S, then n is 2, 3 or 4; and when X is a moiety of formula III and A is $(CR_{17}R_{18})_mS$, then n is 0, 2, 3 or 4. --

UNITED STATES PATENT AND TRADEMARK OFFICE
CERTIFICATE OF CORRECTION

PATENT NO. : 6,228,888 B1
DATED : May 8, 2001
INVENTOR(S) : Barbara S. Slusher

It is certified that error appears in the above-identified patent and that said Letters Patent is hereby corrected as shown below:

Column 53,
Line 18, replace "sulfanylpropyl) pentanedioic acid" with -- 2-(2-sulfanylpropyl) pentanedioic acid --.

Column 54,
Line 1, replace "sulfanylpropyl) pentanedioic acid" with -- 2-(2-sulfanylpropyl) pentanedioic acid --.

Signed and Sealed this

Twenty-fourth Day of December, 2002

JAMES E. ROGAN
*Director of the United States Patent and Trademark Office*